US012653563B2

(12) United States Patent (10) Patent No.: US 12,653,563 B2
Behan (45) Date of Patent: *Jun. 16, 2026

(54) CATHETER APPARATUS AND METHODS FOR ENDOLUMINAL INTERVENTION

(71) Applicant: Julier Medical AG, Dubendorf (CH)

(72) Inventor: Niall Behan, Dubendorf (CH)

(73) Assignee: Julier Medical AG, Dubendorf (CH)

( * ) Notice: Subject to any disclaimer, the term of this patent is extended or adjusted under 35 U.S.C. 154(b) by 309 days.

This patent is subject to a terminal disclaimer.

(21) Appl. No.: 18/586,246

(22) Filed: Feb. 23, 2024

(65) Prior Publication Data

US 2024/0197348 A1 Jun. 20, 2024

Related U.S. Application Data

(63) Continuation of application No. 18/465,120, filed on Sep. 11, 2023, now Pat. No. 11,911,057, which is a
(Continued)

(30) Foreign Application Priority Data

Jan. 30, 2020 (EP) ..................................... 20154527

(51) Int. Cl.
*A61B 17/221* (2006.01)
*A61B 17/00* (2006.01)
*A61B 17/22* (2006.01)

(52) U.S. Cl.
CPC .. *A61B 17/221* (2013.01); *A61B 2017/00778* (2013.01); *A61B 2017/00853* (2013.01);
(Continued)

(58) Field of Classification Search
CPC ..... A61F 2002/0072; A61B 2017/2215; A61B 17/221; A61B 2017/00778; A61B 2017/22079; A61B 17/3439
See application file for complete search history.

(56) References Cited

U.S. PATENT DOCUMENTS 3,868,956 A 3/1975 Alfidi et al.
3,946,741 A 3/1976 Adair
(Continued)

FOREIGN PATENT DOCUMENTS

DE 102011100733 A1 11/2012
EP 0379794 A1 8/1990
(Continued)

OTHER PUBLICATIONS

Alawieh, et al., Impact of Procedure Time on Outcomes of Thrombectomy for Stroke, JACC, 73(8):779-890 (Mar. 2019).
(Continued)

*Primary Examiner* — Katherine H Schwiker
*Assistant Examiner* — Zehra Jaffri
(74) *Attorney, Agent, or Firm* — Greenberg Traurig, LLP; Christopher C. Bolten; Robert D. Ward

(57) ABSTRACT

An apparatus for neurovascular endoluminal intervention, in particular for the treatment of ischemic stroke, is provided. The apparatus comprises a catheter (2) for insertion into the circulatory system (CS) of a patient, in order to aspirate one or several clots (C) present in the circulatory system (CS). A distal outer section (22) of the catheter (2) comprises an unexpanded state, in which the diameter (D2) of the distal outer section (22) is smaller than the diameter (D1) of a proximal outer section (21) of the catheter (2), in order to facilitate navigation of the catheter through the circulatory system, and a radially expanded state, in order to facilitate aspiration of the one or several clots (C) through the catheter (2). Furthermore, a method for applying such an apparatus is provided.

28 Claims, 22 Drawing Sheets

Related U.S. Application Data continuation of application No. 18/131,857, filed on Apr. 6, 2023, now Pat. No. 11,766,272, which is a continuation of application No. 17/812,070, filed on Jul. 12, 2022, now Pat. No. 11,622,781, which is a continuation of application No. PCT/EP2021/051903, filed on Jan. 28, 2021.

(52) U.S. Cl.
CPC .............. *A61B 2017/00867* (2013.01); *A61B 2017/22079* (2013.01); *A61B 2017/2215* (2013.01)

(56) References Cited

U.S. PATENT DOCUMENTS

| | | |
|---|---|---|
| 4,228,802 A | 10/1980 | Trott |
| 4,329,995 A | 5/1982 | Anthracite |
| 4,762,125 A | 8/1988 | Leiman et al. |
| 4,873,978 A | 10/1989 | Ginsburg |
| 4,926,858 A | 5/1990 | Gifford, III et al. |
| 5,011,488 A | 4/1991 | Ginsburg |
| 5,030,201 A | 7/1991 | Palestrant |
| 5,092,839 A | 3/1992 | Kipperman |
| 5,102,415 A | 4/1992 | Guenther et al. |
| 5,234,425 A | 8/1993 | Fogarty et al. |
| 5,256,146 A | 10/1993 | Ensminger et al. |
| 5,318,532 A | 6/1994 | Frassica |
| 5,458,573 A | 10/1995 | Summers |
| 5,695,499 A | 12/1997 | Helgerson et al. |
| 5,776,096 A | 7/1998 | Fields |
| 5,807,311 A | 9/1998 | Palestrant |
| 5,827,243 A | 10/1998 | Palestrant |
| 5,893,869 A | 4/1999 | Barnhart et al. |
| 5,941,869 A | 8/1999 | Patterson et al. |
| 5,972,019 A | 10/1999 | Engelson et al. |
| 6,066,149 A | 5/2000 | Samson et al. |
| 6,159,195 A | 12/2000 | Ha et al. |
| 6,183,492 B1 | 2/2001 | Hart et al. |
| 6,206,868 B1 | 3/2001 | Parodi |
| 6,238,412 B1 | 5/2001 | Dubrul et al. |
| 6,280,464 B1 | 8/2001 | Hayashi |
| 6,319,242 B1 | 11/2001 | Patterson et al. |
| 6,350,271 B1 | 2/2002 | Kurz et al. |
| 6,454,790 B1 | 9/2002 | Neuberger et al. |
| 6,596,011 B2 | 7/2003 | Johnson et al. |
| 6,626,886 B1 | 9/2003 | Barbut |
| 6,632,236 B2 | 10/2003 | Hogendijk |
| 6,679,893 B1 | 1/2004 | Tran |
| 6,685,718 B1 | 2/2004 | Wyzgala et al. |
| 6,685,722 B1 | 2/2004 | Rosenbluth et al. |
| 6,692,504 B2 | 2/2004 | Kurz et al. |
| 6,699,260 B2 | 3/2004 | Dubrul et al. |
| 6,783,522 B2 | 8/2004 | Fischell |
| 6,824,545 B2 | 11/2004 | Sepetka et al. |
| 6,929,634 B2 | 8/2005 | Dorros et al. |
| 7,008,434 B2 | 3/2006 | Kurz et al. |
| 7,220,269 B1 | 5/2007 | Ansel et al. |
| 7,232,452 B2 | 6/2007 | Adams et al. |
| 7,252,674 B2 | 8/2007 | Wyzgala et al. |
| 7,323,002 B2 | 1/2008 | Johnson et al. |
| 7,374,561 B2 | 5/2008 | Barbut |
| 7,399,307 B2 | 7/2008 | Evans et al. |
| 7,645,261 B2 | 1/2010 | Hinchliffe |
| 7,645,296 B2 | 1/2010 | Theron et al. |
| 7,691,121 B2 | 4/2010 | Rosenbluth et al. |
| 7,731,683 B2 | 6/2010 | Jang et al. |
| 7,909,801 B2 | 3/2011 | Hinchliffe |
| 8,100,935 B2 | 1/2012 | Rosenbluth et al. |
| 8,162,878 B2 | 4/2012 | Bonnette et al. |
| 8,292,914 B2 | 10/2012 | Morsi |
| 8,409,237 B2 | 4/2013 | Galdonik et al. |
| 8,425,549 B2 | 4/2013 | Lenker et al. |
| 8,435,218 B2 | 5/2013 | Hinchliffe |
| 8,475,487 B2 | 7/2013 | Bonnette et al. |
| 8,486,104 B2 | 7/2013 | Samson et al. |
| 8,784,441 B2 | 7/2014 | Rosenbluth et al. |
| 8,911,468 B2 | 12/2014 | Ogle et al. |
| 8,956,386 B2 | 2/2015 | Hauser et al. |
| 8,979,870 B2 | 3/2015 | Richardson |
| 9,067,063 B2 | 6/2015 | Chi et al. |
| 9,427,252 B2 | 8/2016 | Sos |
| 9,439,664 B2 | 9/2016 | Sos |
| 9,566,412 B2 | 2/2017 | Ulm, III et al. |
| 9,642,635 B2 | 5/2017 | Vale et al. |
| 9,814,477 B2 | 11/2017 | Jensen |
| 9,848,975 B2 | 12/2017 | Hauser |
| 10,016,266 B2 | 7/2018 | Hauser |
| 10,022,139 B2 | 7/2018 | Kobayashi et al. |
| 10,076,399 B2 | 9/2018 | Davidson |
| 10,080,575 B2 | 9/2018 | Brady et al. |
| 10,105,154 B1 | 10/2018 | Green |
| 10,130,387 B2 | 11/2018 | McRae et al. |
| 10,231,751 B2 | 3/2019 | Sos |
| 10,292,804 B2 | 5/2019 | Wang et al. |
| 10,383,644 B2 | 8/2019 | Molaei et al. |
| 10,433,867 B2 | 10/2019 | Kassab et al. |
| 11,622,781 B2 | 4/2023 | Behan |
| 11,737,767 B2 | 8/2023 | Behan et al. |
| 11,766,272 B2 | 9/2023 | Behan |
| 2001/0011182 A1 | 8/2001 | Dubrul et al. |
| 2002/0013548 A1 | 1/2002 | Hinchliffe |
| 2002/0016624 A1 | 2/2002 | Patterson et al. |
| 2002/0049452 A1 | 4/2002 | Kurz et al. |
| 2002/0082558 A1 | 6/2002 | Samson et al. |
| 2002/0188313 A1 | 12/2002 | Johnson et al. |
| 2004/0006306 A1 | 1/2004 | Evans et al. |
| 2004/0006367 A1 | 1/2004 | Johnson et al. |
| 2004/0049169 A1 | 3/2004 | Fischell |
| 2004/0073243 A1 | 4/2004 | Sepetka et al. |
| 2004/0127885 A1 | 7/2004 | Barbut |
| 2004/0133232 A1 | 7/2004 | Rosenbluth et al. |
| 2004/0153110 A1 | 8/2004 | Kurz et al. |
| 2004/0158270 A1 | 8/2004 | Wyzgala et al. |
| 2005/0027236 A1 | 2/2005 | Douk |
| 2005/0197688 A1 | 9/2005 | Theron et al. |
| 2005/0277976 A1 | 12/2005 | Galdonik et al. |
| 2006/0041246 A1 | 2/2006 | Provost-Tine et al. |
| 2006/0041304 A1 | 2/2006 | Jang et al. |
| 2006/0189921 A1 | 8/2006 | Galdonik et al. |
| 2006/0229645 A1 | 10/2006 | Bonnette et al. |
| 2006/0264989 A1 | 11/2006 | Hinchliffe |
| 2007/0207179 A1 | 9/2007 | Andersen et al. |
| 2008/0015541 A1 | 1/2008 | Rosenbluth et al. |
| 2008/0086110 A1 | 4/2008 | Galdonik et al. |
| 2008/0103508 A1 | 5/2008 | Karakurum |
| 2008/0312681 A1 | 12/2008 | Ansel et al. |
| 2009/0156983 A1 | 6/2009 | Bonnette et al. |
| 2009/0171267 A1 | 7/2009 | Bonnette et al. |
| 2010/0082052 A1 | 4/2010 | Hinchliffe |
| 2010/0131000 A1 | 5/2010 | DeMello et al. |
| 2010/0145371 A1 | 6/2010 | Rosenbluth et al. |
| 2010/0222736 A1 | 9/2010 | Jang et al. |
| 2010/0256600 A1 | 10/2010 | Ferrera |
| 2011/0022075 A1 | 1/2011 | Christiansen et al. |
| 2011/0060298 A1 | 3/2011 | Saadat |
| 2011/0082493 A1 | 4/2011 | Samson et al. |
| 2011/0130778 A1 | 6/2011 | Hinchliffe |
| 2012/0046676 A1 | 2/2012 | Morsi |
| 2012/0271231 A1 | 10/2012 | Agrawal |
| 2013/0190855 A1 | 7/2013 | Wang et al. |
| 2014/0066969 A1 | 3/2014 | Eskridge |
| 2014/0135803 A9 | 5/2014 | Rosenbluth et al. |
| 2014/0200608 A1 | 7/2014 | Brady et al. |
| 2014/0243790 A1 | 8/2014 | Callaghan et al. |
| 2014/0257245 A1 | 9/2014 | Rosenbluth et al. |
| 2014/0276403 A1 | 9/2014 | Follmer et al. |
| 2014/0371769 A1 | 12/2014 | Vale et al. |
| 2014/0371778 A1 | 12/2014 | Rudakov et al. |
| 2015/0032147 A1 | 1/2015 | Janardhan et al. |
| 2015/0088190 A1 | 3/2015 | Jensen |
| 2015/0250497 A1 | 9/2015 | Marks et al. |
| 2015/0359547 A1 | 12/2015 | Vale et al. |
| 2016/0022296 A1 | 1/2016 | Brady et al. |

(56) References Cited

U.S. PATENT DOCUMENTS

| | | | |
|---|---|---|---|
| 2016/0249942 A1 | 9/2016 | Olson | |
| 2016/0249978 A1 | 9/2016 | Lee et al. | |
| 2016/0256180 A1 | 9/2016 | Vale et al. | |
| 2016/0271360 A1 | 9/2016 | Ulm, III | |
| 2016/0338720 A1 | 11/2016 | Kassab et al. | |
| 2016/0361077 A1 | 12/2016 | Marks et al. | |
| 2016/0367285 A1* | 12/2016 | Sos | A61B 17/221 |
| 2017/0105743 A1 | 4/2017 | Vale et al. | |
| 2017/0143938 A1 | 5/2017 | Ogle et al. | |
| 2017/0215903 A1 | 8/2017 | Vale et al. | |
| 2017/0238951 A1 | 8/2017 | Yang et al. | |
| 2017/0303949 A1 | 10/2017 | Ribo Jacobi et al. | |
| 2017/0333060 A1* | 11/2017 | Panian | A61M 25/005 |
| 2017/0333076 A1 | 11/2017 | Bruzzi et al. | |
| 2018/0104041 A1 | 4/2018 | Hauser | |
| 2018/0140315 A1 | 5/2018 | Bowman et al. | |
| 2018/0325647 A1 | 11/2018 | Hauser | |
| 2018/0333248 A1 | 11/2018 | Davidson | |
| 2018/0344248 A1 | 12/2018 | Zeng et al. | |
| 2019/0029713 A1 | 1/2019 | McRae et al. | |
| 2019/0133616 A1 | 5/2019 | Sachar et al. | |
| 2019/0133628 A1 | 5/2019 | Follmer et al. | |
| 2019/0167287 A1 | 6/2019 | Vale et al. | |
| 2019/0269491 A1 | 9/2019 | Jalgaonkar et al. | |
| 2020/0281612 A1 | 9/2020 | Kelly et al. | |

FOREIGN PATENT DOCUMENTS

| | | | |
|---|---|---|---|
| EP | 0385920 | A2 | 9/1990 |
| EP | 0561903 | A1 | 9/1993 |
| EP | 0630617 | A1 | 12/1994 |
| EP | 0561903 | B1 | 7/1995 |
| EP | 0820729 | A1 | 1/1998 |
| EP | 0630617 | B1 | 9/1998 |
| EP | 0961628 | A1 | 12/1999 |
| EP | 0961628 | A4 | 5/2000 |
| EP | 1007130 | A1 | 6/2000 |
| EP | 1007130 | A4 | 6/2000 |
| EP | 1007139 | A1 | 6/2000 |
| EP | 1007139 | A4 | 6/2000 |
| EP | 1026997 | A1 | 8/2000 |
| EP | 1030603 | A1 | 8/2000 |
| EP | 1105183 | A1 | 6/2001 |
| EP | 1105183 | A4 | 3/2002 |
| EP | 1241993 | A1 | 9/2002 |
| EP | 1304965 | A2 | 5/2003 |
| EP | 1030603 | A4 | 6/2003 |
| EP | 1355692 | A1 | 10/2003 |
| EP | 1408854 | A1 | 4/2004 |
| EP | 0961628 | B1 | 12/2004 |
| EP | 1561487 | A2 | 8/2005 |
| EP | 1561487 | A3 | 8/2005 |
| EP | 1026997 | B1 | 10/2005 |
| EP | 1355692 | A4 | 12/2005 |
| EP | 1105183 | B1 | 1/2006 |
| EP | 1611855 | A1 | 1/2006 |
| EP | 1677849 | A1 | 7/2006 |
| EP | 1007130 | B1 | 8/2006 |
| EP | 1691856 | A2 | 8/2006 |
| EP | 1696966 | A2 | 9/2006 |
| EP | 1241993 | B1 | 3/2007 |
| EP | 1761298 | A2 | 3/2007 |
| EP | 1561487 | B1 | 4/2007 |
| EP | 1789121 | A2 | 5/2007 |
| EP | 1791587 | A1 | 6/2007 |
| EP | 2208483 | A1 | 7/2010 |
| EP | 2319575 | A1 | 5/2011 |
| EP | 2786717 | A2 | 10/2014 |
| EP | 2786717 | A3 | 11/2014 |
| EP | 2848211 | A1 | 3/2015 |
| EP | 2851016 | A1 | 3/2015 |
| EP | 3017775 | A1 | 5/2016 |
| EP | 3020344 | A1 | 5/2016 |
| EP | 3718492 | A1 | 10/2020 |
| WO | WO-9306885 | A1 | 4/1993 |
| WO | WO-9823319 | A1 | 6/1998 |
| WO | WO-9823320 | A1 | 6/1998 |
| WO | WO-9834673 | A1 | 8/1998 |
| WO | WO-9836786 | A1 | 8/1998 |
| WO | WO-9916362 | A1 | 4/1999 |
| WO | WO-9923952 | A1 | 5/1999 |
| WO | WO-0012169 | A1 | 3/2000 |
| WO | WO-0145572 | A1 | 6/2001 |
| WO | WO-0187168 | A1 | 11/2001 |
| WO | WO-0209599 | A2 | 2/2002 |
| WO | WO-0239912 | A1 | 5/2002 |
| WO | WO-0209599 | A3 | 7/2002 |
| WO | WO-02055146 | A1 | 7/2002 |
| WO | WO-02087677 | A2 | 11/2002 |
| WO | WO-03097122 | A2 | 11/2003 |
| WO | WO-03097122 | A3 | 6/2004 |
| WO | WO-2005011786 | A1 | 2/2005 |
| WO | WO-2005039664 | A2 | 5/2005 |
| WO | WO-2005039664 | A3 | 6/2005 |
| WO | WO-2005046736 | A3 | 10/2005 |
| WO | WO-2005118050 | A2 | 12/2005 |
| WO | WO-2006023329 | A2 | 3/2006 |
| WO | WO-2006032686 | A1 | 3/2006 |
| WO | WO-2006023329 | A3 | 4/2006 |
| WO | WO-2006110186 | A2 | 10/2006 |
| WO | WO-2006110186 | A3 | 6/2007 |
| WO | WO-2008086180 | A1 | 7/2008 |
| WO | WO-2005118050 | A3 | 1/2009 |
| WO | WO-2009154441 | A1 | 12/2009 |
| WO | WO-2011008987 | A3 | 5/2011 |
| WO | WO-2012156924 | A1 | 11/2012 |
| WO | WO-2014039548 | A1 | 3/2014 |
| WO | WO-2014113821 | A1 | 7/2014 |
| WO | WO-2014188300 | A1 | 11/2014 |
| WO | WO-2015189354 | A1 | 12/2015 |
| WO | WO-2016071524 | A1 | 5/2016 |
| WO | WO-2016113047 | A1 | 7/2016 |
| WO | WO-2016126974 | A1 | 8/2016 |
| WO | WO-2016138260 | A1 | 9/2016 |
| WO | WO-2016138508 | A1 | 9/2016 |
| WO | WO-2017074530 | A1 | 5/2017 |
| WO | WO-2017097616 | A1 | 6/2017 |
| WO | WO-2018033401 | A1 | 2/2018 |
| WO | WO-2018107133 | A1 | 6/2018 |
| WO | WO-2018107133 | A8 | 8/2018 |
| WO | WO-2018169959 | A1 | 9/2018 |
| WO | WO-2018222998 | A1 | 12/2018 |
| WO | WO-2019007032 | A1 | 1/2019 |
| WO | WO-2019027380 | A1 | 2/2019 |
| WO | WO-2019051425 | A1 | 3/2019 |
| WO | WO-2019094749 | A1 | 5/2019 |
| WO | WO-2019094782 | A1 | 5/2019 |
| WO | WO-2019168737 | A1 | 9/2019 |
| WO | WO-2021016213 | A1 | 1/2021 |
| WO | WO-2021151969 | A1 | 8/2021 |

OTHER PUBLICATIONS

Donkor, Eric., Stroke in the 21st Century: A Snapshot of the Burden, Epidemiology, and Quality of Life, Stroke Research and Treatment, vol. 2018, Article ID 3238165 (2018).

Extended European Search Report dated Sep. 27, 2019 in EP Patent Application Serial No. 19167604.8.

Froehler, Michael, Comparison of Vacuum Pressures and Forces Generated by Different Catheters and Pumps for Aspiration Thrombectomy in Acute Ischemic Stroke, Intervent. Neurol, 6(3-4):199-206 (May 2017).

Garcia-Tornel, et al., When to Stop: Detrimental Effect of Device Passes in Acute Ischemic Stroke Secondary to Large Vessel Occlusion, Stroke, 50(7):1781-1788 (Jul. 2019).

International Search Report & Written Opinion dated Apr. 7, 2021 in Int'l PCT Patent Appl. Serial No. PCT/EP2021/051903.

International Search Report & Written Opinion dated Apr. 19, 2023 in Int'l PCT Patent Appl. Serial No. PCT/IB2023/050468.

Jin, et al., Association Between Extracranial Carotid Artery Tortuosity and Clinical Outcomes in Anterior Circulation Acute Ischemic Stroke Without Undergoing Endovascular Treatment, Journal of

(56) References Cited

OTHER PUBLICATIONS

Stroke and Cerebrovascular Diseases, 29(2):104512 (Feb. 2020).

Kaymaz, et al., Influence of Carotid Tortuosity on Internal Carotid Artery Access Time in the Treatment of Acute Ischemic Stroke, Interventional Neuroradiology, 23(6):583-588 (Dec. 2017).

Mokin, et al., Semi-automated Measurement of Vascular Tortuosity and its Implications for Mechanical Thrombectomy Performance, Neuroradiology, 63(3):381-389 (Mar. 2021).

Mont'Alverne, et al., Unfavorable Vascular Anatomy During Endovascular Treatment of Stroke: Challenges and Bailout Strategies, Journal of Stroke: 22(2):185-202 (May 2020).

Pfaff, et al., Delivery Assist Catheters, A New Device Class and Initial Experience in Mechanical Thrombectomy in Acute Ischemic Stroke Patients, Clinical Neuroradiology, 29(4):661-667 (Dec. 2019).

Rosa, et al., Aortic and Supra-Aortic Arterial Tortuosity And Access Technique: Impact on Time to Device Deployment in Stroke Thrombectomy, Interventional Neuroradiology, 27(3):419-426 (Jun. 2021).

Sanchez, et al., ANCD Thrombectomy Device: In Vitro Evaluation, J. NeuroIntervent. Surg., 12(1):77-81 (Jan. 2020).

Snelling, et al., Unfavorable Vascular Anatomy Is Associated With Increased Revascularization Time and Worse Outcome in Anterior Circulation Thrombectomy, World Neurosurgery, 120:e976-83 (Dec. 2018).

Yeo, et al., Why Does Mechanical Thrombectomy in Large Vessel Occlusion Sometimes Fail?, Clinical Neuroradiology, 29(3):401-414 (Sep. 2019).

\* cited by examiner

23

23

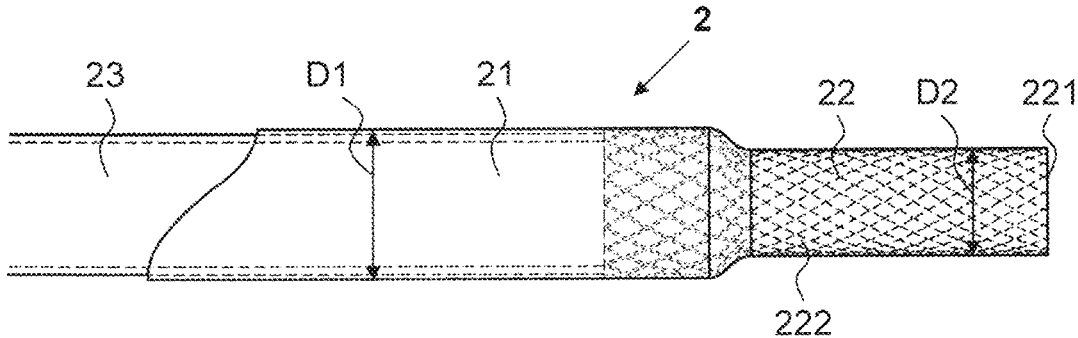
FIG. 5a
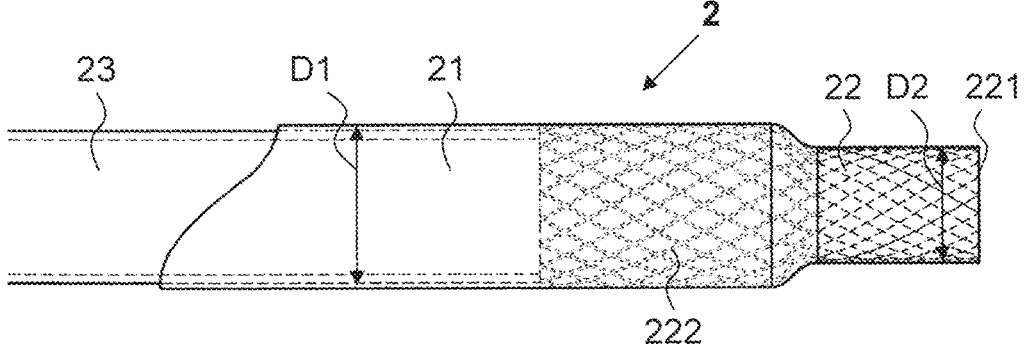
FIG. 5b
FIG. 5c

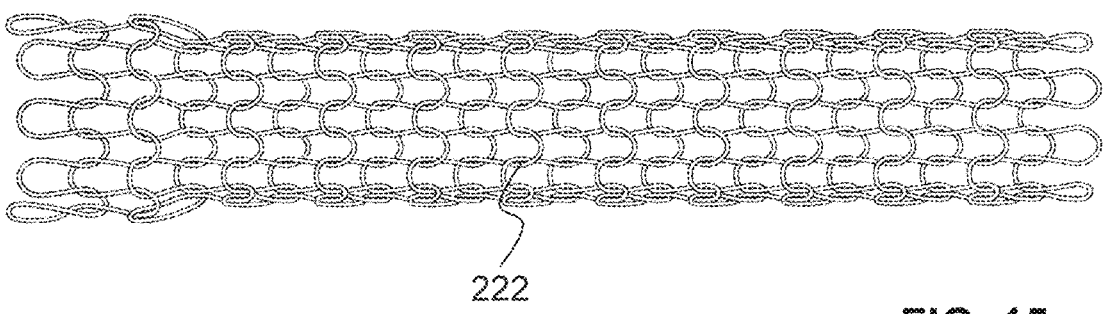
222
FIG. 15
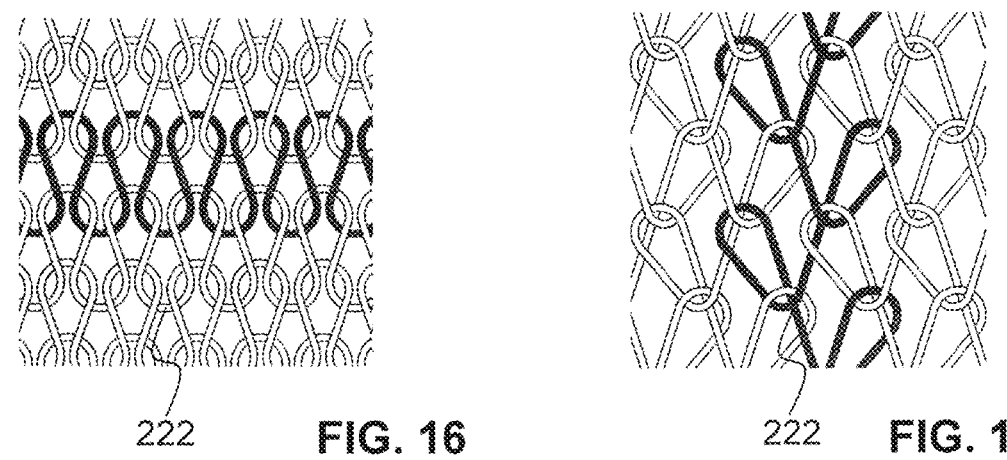
222     FIG. 16          222     FIG. 17
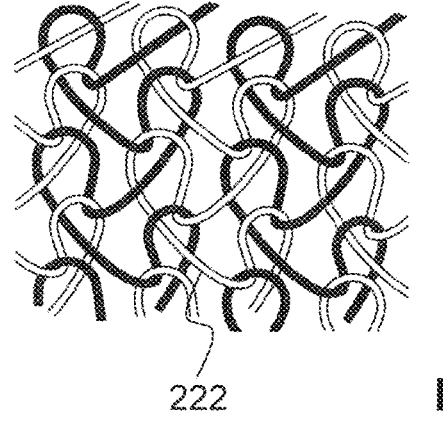
222          FIG. 18

222

222

222

222

222

222

CATHETER APPARATUS AND METHODS FOR ENDOLUMINAL INTERVENTION

CROSS-REFERENCE TO RELATED APPLICATIONS

This application is a continuation of U.S. patent application Ser. No. 18/465,120, filed Sep. 11, 2023, now U.S. Pat. No. 11,911,057, which is a continuation of U.S. patent application Ser. No. 18/131,857, filed Apr. 6, 2023, now U.S. Pat. No. 11,766,272, which is a continuation of U.S. patent application Ser. No. 17/812,070, filed Jul. 12, 2022, now U.S. Pat. No. 11,622,781, which is a continuation of International PCT Patent Application Serial No. PCT/EP2021/051903, filed Jan. 28, 2021, which claims the benefit of priority of EP Patent Application Serial No. 20154527.4, filed Jan. 30, 2020, the entire contents of each of which are incorporated herein by reference.

TECHNICAL FIELD

The present invention relates to an apparatus and a method for neurovascular endoluminal intervention, in particular for the treatment of ischemic stroke. The apparatus can particularly be referred to as a clot retrieval apparatus for the removal of a clot from a blood vessel and the method as a method for the retrieval of a clot from a blood vessel.

PRIOR ART

Ischemic stroke is caused by a partial or complete interruption to cerebral blood perfusion. Such an interruption can be caused by a thrombus or embolus, i.e. a clot, originating from a more proximal location with the bloodstream, becoming trapped within the narrowing intracranial vessels. The interruption of blood flow to a portion of the brain for any prolonged period of time results in a region of infarcted tissue, known as the core infarct, that is irreversibly damaged and grows larger with time. Infarcted regions of the brain will result in neurological deficits that can range from minor speech and coordination problems to total loss of muscle and cognitive control.

The oxygen-starved region around the core infarct also grows larger, the longer the interruption continues. This region, known as the penumbra can be regenerated, if blood perfusion is restored in a timely manner. This phenomenon of a treatable ischemic event has given rise to the phrase "time is brain", now common amongst associated clinicians.

In recent years, the technology for mechanical removal of such blockages has enabled reperfusion of blood flow and effective treatment of stroke in some cases. Within the last years, the first of several clinical studies were published that validated the efficacy of stent retrievers for blood flow restoration versus the standard of care at the time, which was intravenous thrombolysis medication and aspiration clot retrieval.

Mechanical clot retrieval devices are for example metal baskets or stents that are connected to a retrieval wire. During a clot removal procedure, a guide wire is placed across the length of the clot and a catheter is navigated over the guidewire to cross the clot. The clot retrieval device is delivered through the catheter to the required location. The catheter or sheath is retracted from over the clot retrieval device, which then expands and engages with the clot. The clot retrieval device and the clot integrated therein can then be removed through the blood vessel using tension by pulling the retrieval wire. Optionally, a suction catheter can be used to help with removal.

In many cases, the clot cannot be removed intact during the first pass of the clot retrieval device and multiple passes are required to get blood flow restoration. The improvement in first pass clot removal is a target of many current developments in this field of technology.

In practice, the clinician will use several different tools during the endovascular procedure to remove the clot. Generally, a guidewire will be placed into the femoral artery using the modified Seldinger technique and will be navigated through the carotid artery into the cerebral vasculature of the brain.

The guidewire is then pushed through the clot. Once the guidewire is in place, a very narrow tubular catheter known as a microcatheter (approx. 0.4 mm diameter) is advanced to the distal side of the clot over the wire.

The guidewire is then removed and a stent retriever is pushed through the microcatheter and deployed along the length of the clot. The stent retriever engages with the clot and is then retracted, in order to remove the clot from the circulatory system of the patient. In most cases, this procedure is carried out while simultaneously applying aspiration through a larger diameter catheter that is navigated close to the clot over the microcatheter. The aspiration catheter is stiffer than the microcatheter due to its larger diameter and reinforcement, which is required to prevent collapse during suction. The microcatheter is therefore also required as a support and guide for introduction of the aspiration catheter through the vasculature.

The yet unpublished European patent application EP 19 167 604.8 of the same applicant discloses a catheter apparatus for the removal of a clot from the circulatory system of a human or an animal patient, in which a plurality of clot-engaging element can be deployed independently from each other. In this way, the first pass clot removal rate can be improved.

In addition to the above technique there have been multiple different approaches described using the combination of stent retriever and aspiration catheter. Some of these techniques describe the complete withdrawal of stent retriever and clot into the aspiration catheter. Other approaches are directed to the withdrawal of the clot and stent retriever by means of the aspiration catheter, wherein the proximal part of the clot is attached to the aspiration catheter during the removal.

The clot retrieval approach chosen is often influenced by the clot composition and in some cases where the clot is e.g. a very soft thrombus, an aspiration catheter alone is sufficient to remove the entire clot via suction. In this case, a microcatheter is still required for support to help with navigation of the aspiration catheter to the desired site.

Regardless of the specific technique used, removal of the clot without delay is crucially important. Although the guidewire and microcatheter are generally advanced to the clot quickly, the positioning of the aspiration catheter can be a limiting factor. The process of advancing the aspiration catheter becomes particularly difficult after passing through the internal carotid artery. This is due to the narrow and tortuous vessels after this point in the cerebral vasculature and is exacerbated in older patients where the vasculature is diseased and elongated. This time-consuming part of the procedure can impact the patients clinical outcome. In the case where the clot is not removed during the first pass, the cumulative time taken during multiple attempts can be significant.

It is known to arrange a device with a distally expanding funnel at the distal end of the aspiration catheter. These devices are generally separate to the aspiration catheter and are fed through the lumen and pushed out of the distal end of the aspiration catheter to expand. Such devices are intended to widen the already large luminal diameter of the aspiration catheter and to engulf a withdrawing stent retriever and/or clot to ensure no microemboli are released during the clot removal. WO 02/087677 A2, US 2017/0303949 A1, WO 2016/113047 A1, US 2019/0269491 A1, US 2017/0333060 A1 are examples of documents directed to this kind of technique.

WO 2017/097616 A1 discloses a plurality of devices and methods for removing blockages from blood vessels. According to a first embodiment shown in FIGS. 1 to 2f of this document, a stent retriever is first deployed by means of a microcatheter. In order to improve the clot removal process, an aspiration catheter is then advanced to the position of the clot.

By means of the aspiration catheter, a clot receptor device is deployed, which circumferentially seals against a distal section of the aspiration catheter, such that the stent retriever and the clot can be aspirated through the tapered opening of the receptor device during the removal process. In another embodiment shown in FIGS. 10 to 11d of the same document, the stent retriever is also deployed by means of a microcatheter. An aspiration catheter is then forwarded to the position of the clot, in order to aspirate the stent retriever and the clot. The distal tip of the aspiration catheter is proposed to be expansile, in order to form a tapered opening for facilitating the reception of the clot in the aspiration and removal process.

U.S. Pat. No. 8,425,549 B2 discloses a catheter having a distal portion, which can be radially expanded by means of a coil or a helical ribbon that is distally displaceable within the catheter. The expanded configuration allows applying a negative pressure through the lumen of the catheter, in order to aspirate obstructive matter through the distal end opening and into the lumen of the catheter.

Further devices for neurovascular endoluminal intervention of the kind as indicated are disclosed in WO 2016/126974 A1, WO 2018/169959 A1 and WO 98/23320 A1.

Besides the above-described catheter devices, introducer sheaths are known, which are short cannula-like devices that are used for vessel access. They are inserted into the target vessel percutaneously and a central dilator is then removed to allow access for insertion of other devices such as guidewires and catheters. Recently a number of introducer devices have been developed that have the capability to expand to accommodate devices larger than the nominal vessel size. Examples of expanding sheath type devices are the Edwards eSheath™ and the Terumo Solopath™.

SUMMARY OF THE INVENTION

It is an object of the present invention to provide an apparatus for neurovascular endoluminal intervention, in particular for the treatment of ischemic stroke, which allows an overall easier and faster removal of a clot from a blood vessel.

This object is solved by an apparatus as claimed in claim 1. Further embodiments of the apparatus are provided in dependent claims 2 to 15. A method for neurovascular endoluminal intervention, which can particularly be used in combination with an apparatus as claimed in claim 1, is provided in claim 16.

The present invention provides an apparatus for neurovascular endoluminal intervention, in particular for the treatment of ischemic stroke, more particularly for the removal of a clot from the circulatory system of a human or an animal patient, comprising a catheter for being inserted, along of its longitudinal length, into the circulatory system of a human or an animal patient, the catheter having a proximal outer section with a first diameter and a distal outer section with a second diameter, wherein the catheter is adapted to aspirate one or several clots present in the circulatory system.

The distal outer section of the catheter comprises an unexpanded state, in which the second diameter is smaller than the first diameter, in order to facilitate navigation of the catheter through the circulatory system. Furthermore, the distal outer section of the catheter comprises a radially expanded state, in order to facilitate aspiration of the one or several clots through the catheter.

Thus, in the apparatus as indicated, a microcatheter and an aspiration catheter are combined into one catheter. The catheter has two states or configurations—a first configuration whereby the catheter has a relatively wide proximal outer section, approximately wide enough to function as an aspiration catheter and a narrow distal outer section that functions as a microcatheter. In this first configuration, the distal outer section is adapted to be easily navigated through the vasculature. The catheter can then, preferably reversibly, be changed to a second state or configuration whereby the distal outer section is expanded to a wider diameter, preferably approximately equivalent to the diameter of the proximal outer section. This approach enables the catheter to be easily and rapidly navigated to the target site and subsequently dilated to facilitate removal of the one or several clots by aspiration. Using this design, a clinician does not waste valuable time navigating a large aspiration catheter through tortuous vessels. In addition, the combination of a microcatheter and an aspiration catheter into a single catheter may also represent a cost saving.

The catheter is preferably adapted to be inserted into the femoral artery of an ordinary adult human patient and to be navigated to the brain, in particular to the middle cerebral artery, of the patient. Thus, the length of the catheter is preferably such that the catheter can at least extend from the femoral artery of an ordinary adult human patient to the brain, in particular to the middle cerebral artery, of the same patient. Depending on the application (e.g. in animals or humans, in children, female or male adults etc.) the catheter preferably has an overall length of at least 30 cm, more preferably of at least 40 cm. For the use in humans, in particular in adult humans, the overall length of the catheter is preferably in a range between 100 cm and 200 cm, more preferably in a range between 130 cm and 180 cm.

Along of its longitudinal extension, the catheter has a proximal outer section and a distal outer section, which are preferably arranged directly behind each other along the longitudinal direction of the catheter and particularly directly merge into each other via a transition. The proximal outer section defines a first diameter, preferably an outer diameter of the catheter, and the distal outer section defines a second diameter, which preferably is also an outer diameter of the catheter. The second diameter of the distal outer section changes in length depending when the distal outer section is brought from its unexpanded state into its expanded state or vice versa.

In the expanded state, the second diameter of the distal outer section is preferably enlarged as compared to the unexpanded state. From the unexpanded state of the distal outer section to the expanded state, the second diameter preferably increases by a multiple of at least 1.5, more preferably a multiple of at least 2 and most preferably a multiple of at least 3. The first diameter of the proximal outer section preferably remains unchanged when the distal outer section is brought from its unexpanded in its expanded state.

In absolute terms, the second diameter of the distal outer section is, in the unexpanded state, in a preferred range between 0.1 and 1 mm, more preferably between 0.1 and 0.8 mm, even more preferably between 0.2 and 0.6 mm and most preferably between 0.3 and 0.5 mm, in particular approximately 0.4 mm. In the expanded state, the second diameter of the distal outer section is preferably in a range between 1 and 2 mm, more preferably between 1.2 and 1.8 mm, most preferably between 1.4 and 1.6 mm, in particular approximately 1.5 mm.

In the unexpanded state, the second diameter of the distal outer section is preferably by at least 30%, more preferably by at least 50%, and most preferably by at least 70% smaller than the first diameter of the proximal outer section.

Preferably, the catheter is designed such that the second diameter of the distal outer section cannot be expanded beyond the first diameter of the proximal outer section.

The term "clot" refers to an obstacle in a blood vessel of the circulatory system of a human or an animal patient, which needs to be removed, in order to enable a free bloodstream in the respective blood vessel. A clot can for example be a thrombus or embolus originating from a more proximal location within the bloodstream, such as from the heart of the lung, which has become trapped within the narrowing intracranial vessels, i.e. within the neurovascular system of the patient.

In a particularly preferred embodiment, the apparatus additionally comprises a clot-retriever adapted to be positioned in the circulatory system by means of the catheter, in order to engage with the one or several clots present in the circulatory system and to be retracted into the expanded distal outer section of the catheter. The apparatus is preferably adapted to retract the clot-retriever while simultaneously aspirating the one or several clots through the catheter. In this way, the clot removal is particularly reliable and safe.

The clot-retriever can particularly have the form of a stent-retriever. Advantageously, the clot-retriever is connected to a retrieval wire that extends through the entire catheter and serves to actuate the clot-retriever, in particular to retract the clot-retriever with the one or several clots from the vasculature.

In certain embodiments, the clot-retriever can comprise a plurality of clot-engaging elements. If a plurality of clot-engaging elements are provided, they can be adapted to be deployed independently from each other as in the apparatus disclosed in the yet unpublished European patent application EP 19 167 604.8 of the same applicant, the entire disclosure of which is hereby incorporated by reference.

The clot-retriever preferably comprises an unexpanded state and a radially expanded state. In the unexpanded state, the clot-retriever usually has an outer radial diameter, which preferably is a multiple smaller than the outer radial diameter in the expanded state. Thus, the clot-retriever is preferably adapted to radially expand upon deployment, which means that the radial extension of the clot-retriever increases. By means of the expansion, at least a part of the clot-retriever engages with the clot directly or when being retracted. In the unexpanded state, the clot-retriever can be inserted in the catheter, in order to be positioned in the circulatory system and in particular to be brought to the region of the clot, by means of the catheter. Thus, in the unexpanded state, the clot-retriever is preferably arranged within the catheter and held in place by the latter, such that the clot-retriever moves with the catheter.

The clot-retriever is preferably at least partially made from an elastic metal such as Nitinol or from another alloy which is commonly used for stent production. The clot-retriever preferably comprises one or more stent-like structures that can be laser cut from Nitinol or from another super-elastic metal.

The clot-retriever is preferably brought from its unexpanded in its expanded state owing to its elasticity. Thus, the clot-retriever can advantageously be reversibly collapsed, for example, when required to be loaded into the catheter. In the unexpanded state, the clot-retriever is preferably pre-stressed along the radial direction. The expansion is then preferably carried out by moving a radially limiting element, i.e. the catheter, at least partially away from the clot-retriever which by doing so is allowed to radially expand owing to its elastic properties.

In the expanded state of the distal outer section, the second diameter of the distal outer section is preferably approximately the same than the first diameter of the proximal outer section. In this way, aspiration of the clot(s) can be optimally carried out through the proximal and distal outer sections. In some embodiments, the second diameter can even be larger than the first diameter in the expanded state of the distal outer section, e.g. for facilitating retraction of the clot-retriever and/or the clot(s) into the catheter.

In a particularly preferred embodiment, the distal outer section has a cylindrical shape in the unexpanded state and/or in the expanded state. A cylindrical shape of the distal outer section not only facilitates navigation of the catheter through the vasculature, but is also advantageous to firmly hold the clot-retriever along of its entire longitudinal extension inside of the distal outer section during the positioning process. Advantageously, the distal outer section has a cylindrical shape along of essentially its entire longitudinal length. The overall longitudinal length of the distal outer section is preferably more than 1 cm, more preferably more than 2 cm and most preferably more than 3 cm. In certain embodiments, the length of the distal outer section can even be more than 5 cm, 10 cm or 15 cm. In a particularly preferred embodiment, the distal outer section has a length in a range between 15 cm and 20 cm.

The distal outer section advantageously comprises at least one reinforcement element, in particular a braided structure or a knitted structure or a crochet structure, which is adapted to radially expand, when being longitudinally compressed, and/or to radially contract, when being longitudinally stretched, and/or to radially expand, when being longitudinally stretched, and/or to radially contract, when being longitudinally compressed. The radial expansion or contraction upon a change in length of the reinforcement element is preferably reversible. Thus, the distal outer section of the catheter can in this case be brought from the unexpanded state to the expanded state, and preferably vice versa, by means of longitudinally compressing (or longitudinally stretching) the at least one reinforcement element. In other words, the at least one reinforcement element is adapted to convert a longitudinal movement of e.g. an actuation element into a radial expansion and/or a radial contraction of the distal outer section. For longitudinally compressing and/or stretching the at least one reinforcement element, an actuation element is preferably attached or attachable to the proximal or distal end of the distal outer section, in particular of the at least one reinforcement element. The other of the distal or proximal end is preferably stationary with respect to the proximal outer section. Advantageously, the actuation element is releasably attached or is releasably attachable to the at least one reinforcement element, in particular to the proximal or distal end of the at least one reinforcement element. A releasable attachment allows the actuation element to be removed from the catheter, e.g. after expanding the distal outer section. The actuation element can be a push element or a pull element. The push element can for example be in the form of a push thread or wire, a push tube or a push coil. The pull element can accordingly for example be in the form of a pull thread or wire, a pull tube or a pull coil.

In a particularly preferred embodiment, the actuation element has the form of a push tube and the apparatus additionally comprises a trailing wire, which is attached to the distal end of the at least one reinforcement element and extends within the push tube. By longitudinally moving the push tube along the distal direction to the point where the trailing wire is attached to the at least one reinforcement element, or even further, the push tube can be locked to the at least one reinforcement element via the trailing wire, so that the at least one reinforcement element can be longitudinally stretched by the push tube. This embodiment has the particular advantage that the actuation element can be locked to and released from the reinforcement element as often as required. Of course in an alternative embodiment it would also be possible to attach the trailing wire to the proximal end of the at least one reinforcement element, in order to longitudinally compress the at least one reinforcement element by means of the push tube locked to the trailing wire.

The at least one reinforcement element, which preferably is in the form of a braided structure, advantageously also serves to prevent kinking of the catheter, in particular during navigation of the catheter through the vasculature and during aspiration of the clot(s), in order to prevent the catheter from collapsing. The at least one reinforcement element can particularly form a structural support element of the distal outer section. The alt least one reinforcement element particularly serves to prevent collapse of the distal outer section of the catheter during suction. According to a preferred embodiment, the at least one reinforcement element is covered.

The distal outer section is preferably adapted not only to be brought from its unexpanded state to its expanded state, but also from its expanded state to its unexpanded state. The change from the unexpanded to the expanded state and vice versa can preferably be carried out actively, e.g. by means of an actuation element, by the clinician.

In another embodiment, the catheter additionally comprises an inner tubular element, in particular an inner tube, which can be longitudinally moved relative to the distal outer section, in order to bring the distal outer section from its unexpanded state into its expanded state. Thus, the inner tubular element advantageously serves as an actuation element for the clinician. The inner tubular element preferably defines the inner lumen of the catheter along of essentially the entire length of the catheter. By forwarding an inner tubular element to expand the distal outer section, a particularly smooth inner and outer transition between the proximal and the distal outer sections can be achieved, when the distal outer section is in its expanded state. Thus, the distal outer section can preferably be expanded by pushing the inner tubular element into the inner lumen of the distal outer section.

The distal outer section is preferably made from an elastic material, which keeps the distal outer section in its unexpanded state, if the inner tubular element is arranged coaxially and proximally of the distal outer section, and which is radially stretched outwardly, if the inner tubular element is moved coaxially into the distal outer section. Owing to its elasticity, the distal outer section preferably automatically returns into its unexpanded state, if the inner tubular element is retracted again from the distal outer section.

Alternatively, the distal outer section can comprise a braided structure and an outer hull, the braided structure being attached to the inner tubular element, in particular to the distal end of the inner tubular element, with a first end and to a distal end of the outer hull with a second end. The braided structure is then preferably adapted to radially expand, when being longitudinally compressed by moving the inner tubular element towards the distal end of the outer hull.

The inner tubular element can comprise or be formed by a hypotube or by a coil which preferably extends along the entire longitudinal length of the inner tubular element. The windings of the coil are preferably lying directly next to each other, such that there are no gaps between adjacent windings. Thus, the coil is preferably tightly wound. The construction of the inner tubular element as a coil is advantageous with regard to the desired flexibility of the inner tubular element tube on the one hand and to its resistivity against kinking and collapsing during aspiration on the other hand. The inner tubular element may be coated with a low friction coating such as PTFE or Parylene. In another embodiment, the inner tubular element can also be in the form of a continuous wire forming structures that extend in alternating circumferential directions over at least a part of the circumference in each case. In yet another embodiment, the inner tubular element can be in the form of a plurality of C- or O-shaped elements that are attached, in particular welded, to a longitudinally extending wire.

In the unexpanded state of the distal outer section, advantageously also in the expanded state, the transition of the catheter from the proximal outer section to the distal outer section is preferably defined by a continuously, i.e. gradually without abrupt changes or discontinuities, decreasing outer diameter and/or inner diameter. Sharp inner and/or outer edges that might cause vasculature damage during catheter navigation or aerodynamic turbulences during aspiration can be avoided in this way.

The apparatus preferably comprises an actuation element by which the clinician can change the state of the distal outer section actively from the unexpanded state into the expanded state, and advantageously vice versa as well. As already mentioned above, such an actuation element can for example be in the form of a push or a pull element or in the form of an inner tubular element, in particular an inner tube, that is movable with respect to the distal outer section. The actuation element can, however, also have a different form. In certain embodiments, the actuation element can be attached to the proximal or distal end of the distal outer section, and the distal outer section can in this case be adapted to be brought from its unexpanded state into its expanded state upon actuation of the actuation element. For example, the actuation element can be a pull element, such as a pull thread, and the distal outer section can be adapted to be brought from its unexpanded state into its expanded state, if the distal end is pulled in the proximal direction by the pull element. In this case, the distal outer section is preferably pressed towards the proximal outer section by the pulling element, in order to be longitudinally compressed. Due to this longitudinal compression, the distal outer section is radially expanded, which can be caused by e.g. a braided structure of the distal outer section. In another embodiment, the actuation element can be a push element, such as a push thread having a certain stiffness against bending, and the distal outer section can be adapted to be brought from its expanded state into its unexpanded state, if the distal end is pushed in the distal direction by the push element. In this case, the distal end of the distal outer section is preferably pushed away from the proximal outer section by the push element, such as to longitudinally stretch the distal outer section. Due to this longitudinal stretching, the distal outer section is radially contracted, which can be caused by e.g. a braided structure of the distal outer section. In another embodiment, the actuation element can also be a tubular structure and can be reversibly attached to the distal end of the distal outer section. The reversible attachment may be achieved using means such as a weak adhesive bond, a magnetic attachment or friction caused by the compressive force of the elastic outer hull.

In another alternative embodiment, the actuation element can be a coiled thread, which is adapted to radially expand in the region of the distal outer section, when being longitudinally compressed. The coiled thread is preferably made of a memory-shape material, in particular a memory-shape allow, such as nitinol (NiTi).

Of course, the above-mentioned actuation elements, i.e. the inner tubular element, the push element, the pull element and the coiled thread, can also be combined, in order to facilitate the expansion of the distal outer section.

In order to facilitate navigation of the catheter through the circulatory system and to prevent endoluminal damages, a lubricious coating is preferably provided on the outer surface of the catheter and in particular on the outer surface of the distal outer section.

Furthermore, the current invention is directed to a method for neurovascular endoluminal intervention, by means of an apparatus comprising a catheter having a proximal outer section with a first diameter and a distal outer section with a second diameter, in particular by means of an apparatus as described above. The method comprises at least the steps of a.) inserting the catheter along of its longitudinal length into the circulatory system of a human or an animal patient; and b.) aspirating one or several clots present in the circulatory system through the catheter.

The distal outer section of the catheter used in this method comprises an unexpanded state, in which the second diameter is smaller than the first diameter, and a radially expanded state. During step a.), the distal outer section is in its unexpanded state, in order to facilitate navigation of the catheter through the circulatory system. During step b.), the distal outer section is in its expanded state.

The method steps a.) and b.) as mentioned above are preferably carried out in the consecutive order as indicated, in particular one after each other.

Thus, after insertion of the catheter into the circulatory system, the distal outer section of the catheter is brought from its unexpanded into its expanded state, in order to facilitate aspiration of the one or several clots through the catheter.

The distal outer section of the catheter used in the method preferably comprises an unexpanded state, in which the second diameter is smaller than the first diameter, and a radially expanded state, in which the second diameter can particularly be the same as the first diameter. In this case, the catheter is preferably inserted in step a.) with the distal outer section being in its unexpanded state, in order to facilitate navigation of the catheter through the circulatory system. In step b.), the one or several clots are preferably aspirated with the distal outer section being in its expanded state. Furthermore, the distal outer section of the catheter used in the method advantageously comprises at least one reinforcement element, in particular a braided structure, which is adapted to radially expand, when being longitudinally compressed, and/or to radially contract, when being longitudinally stretched.

The apparatus preferably also comprises a clot-retriever which is positioned, i.e. deployed, in the circulatory system by means of the catheter in a further method step between steps a.) and b.), in order to engage the clot-retriever with the one or several clots present in the circulatory system. During the aspiration in step b.), the clot-retriever is preferably simultaneously retracted into the catheter.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings.

FIG. 1c shows a variant of an inner tubular element that can be used in combination with the catheter of FIG. 1a;

FIG. 5a shows a side view of a catheter of an apparatus according to a fifth embodiment of the invention, with partially cut open outer hull, in the unexpanded state of the distal outer section;

FIG. 5b shows the catheter of FIG. 5a, in a partially expanded state of the distal outer section;

FIG. 5c shows the catheter of FIG. 5a, in the expanded state of the distal outer section;

FIG. 9b shows a perspective view of the distal end part of the push element used in combination with the catheter of FIG. 9a;

FIG. 15 shows a reinforcement element for a catheter of an inventive apparatus, in the form of a knitted structure;

FIG. 16 shows a first variant of a knitting pattern of a knitted reinforcement element for a catheter of an inventive apparatus;

FIG. 17 shows a second variant of a knitting pattern of a knitted reinforcement element for a catheter of an inventive apparatus;

FIG. 18 shows a crochet pattern of a crocheted reinforcement element for a catheter of an inventive apparatus;

DESCRIPTION OF PREFERRED EMBODIMENTS

Figure 1A:
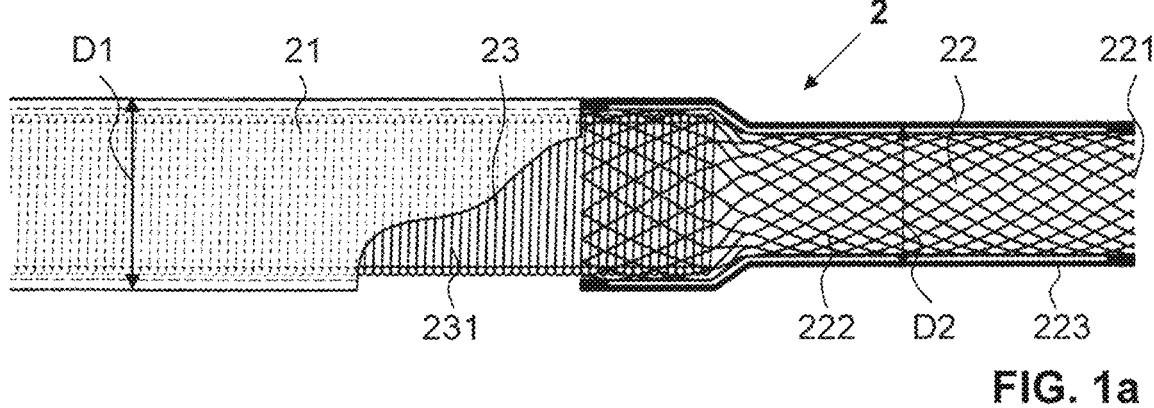
FIG. 1a shows a side view of a catheter of an apparatus according to a first embodiment of the invention, with partially cut open outer hull, in the unexpanded state of the distal outer section.

In the figures, elements of differing embodiments, but having an identical or similar functioning and/or design are indicated by means of the same reference numerals.

In FIGS. 1a to 23, a plurality of embodiments and variants of inventive apparatuses and in particular catheters of such apparatuses for neurovascular endoluminal intervention, in particular for the treatment of ischemic stroke, are shown.

Figure 1B:
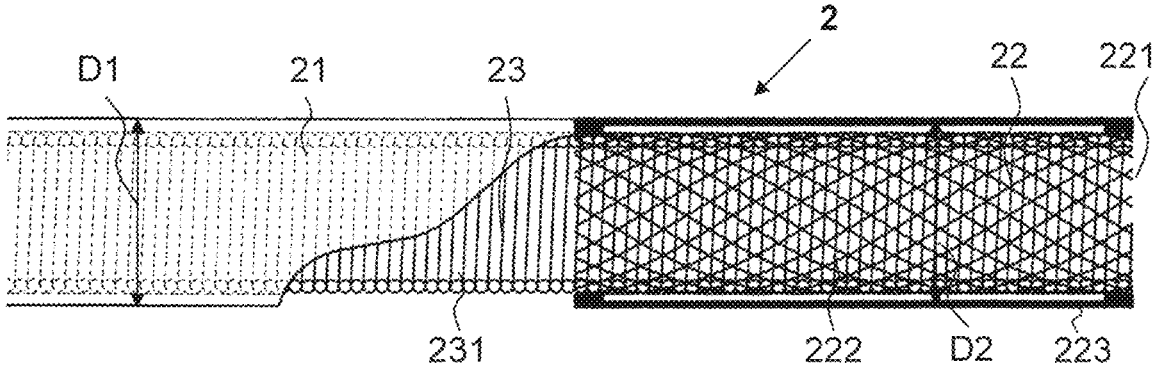
FIG. 1b shows the catheter of FIG. 1a, in the expanded state of the distal outer section.

FIGS. 1a and 1b show a first embodiment of a catheter 2 of an inventive clot retrieval apparatus. The catheter 2 generally has an overall tubular structure, in order to be inserted, along of a major part of its entire longitudinal length, into the circulatory system of a human or animal patient. Through an inner lumen of the catheter 2, a variety of devices, in particular a clot-retriever, can be forwarded to the site of interruption of a cerebral blood vessel.

The catheter 2 comprises a proximal outer section 21 and a distal outer section 22. The longitudinal length of the proximal outer section 21 is usually by a multiple greater than the one of the distal outer section 22. The distal outer section 22 is directly connected to the proximal outer section 21. The proximal outer section 21 preferably forms a proximal end (not shown in the figures) of the catheter 2, which usually remains outside of the patient during the intervention. The proximal end comprises a first opening which gives access to the inner lumen of the catheter 2. A distal end 221 of the catheter 2 is formed by the distal outer section 22. The distal end 211 comprises a second opening which gives access to the inner lumen of the catheter 2. Apart from the first and second openings at the proximal and distal ends, the catheter preferably has no further openings. Thus, the catheter 2 is able to forward an aspiration force from the first opening at the proximal end to the second opening at the distal end.

The proximal outer section 21 and the distal outer section 22 form the radially outermost parts of the catheter 2. In the current embodiments, an elastic hull 223 completely covers both the proximal outer section 21 and the distal outer section 22. Radial collapse of the catheter 2 is prevented in the proximal outer section 21 by an inner tubular element 23. The inner tubular element 23 is completely, i.e. along its entire length, covered to the outside by the elastic hull 223. The inner tubular element 23 is here, i.e. in the present embodiment, formed by a tightly wound coil 231. The design of the inner tubular element 23 in the form of a coil 231 allows the catheter 2 on the one hand to have a desired flexibility for the navigation through the vasculature. On the other hand, the coil 231 gives the catheter 2 a certain radial resistance, which prevents the catheter 2 from radially collapsing, if an aspiration force, i.e. a vacuum, is applies through its inner lumen. Instead of comprising a coil 231, the inner tubular element 23 could also be formed by as hypotube as known in the art.

As can be seen from a combined view of FIGS. 1a and 1b, the distal outer section 22 of the catheter 2 has an unexpanded state (FIG. 1a) and a radially expanded state (FIG. 1b). The distal outer section 22 has an outer diameter D2 that is substantially increased, when the distal outer section 22 is brought from its unexpanded into its radially expanded state. Also the inner diameter, i.e. the diameter of the inner lumen, of the distal outer section 22 is substantially increased in the expanded state as compared to the unexpanded state.

In order to bring the distal outer section 22 into the expanded state, the inner tubular element 23 needs to be forwarded with respect to the proximal and distal outer sections 21, 22 and in particular with respect to the outer hull 223 by the clinician. Thus, the inner tubular element 23 is movable along the longitudinal direction with respect to the proximal and distal outer sections 21, 22. By forwarding the inner tubular element 23 into the distal outer section 22, the overall elastically designed distal outer section 22 is radially expanded to have, in the expanded state, the same diameter D2 as the diameter D1 of the proximal outer section 21. If the inner tubular element 23 is retracted, the distal outer section 22 again returns to its unexpanded state owing to the elasticity of the outer hull 223.

In order to achieve sufficient radial stiffness and at the same time allow the distal outer section 22 to bend, a reinforcement element 222 is provided as part of the distal outer section 22. The reinforcement element 222 is here formed by a braided structure of the distal outer section 22. In the unexpanded state, which is adopted during the insertion process of the catheter 2 into the circulatory system, the reinforcement element 222 gives the distal outer section the required flexibility for being navigated through the vasculature of the patient. In the expanded state, the reinforcement element 222 prevents radial collapse of the distal outer section 22 during the aspiration process.

In both the expanded and the unexpanded state, the outer diameters D1 and D2 are constant along the entire length of the respective proximal or distal outer section 21, 22. Thus, in both the expanded and the unexpanded state, each of the proximal outer section 21 and the distal outer section 22 have, as a whole, the form a hollow cylinder. The diameter D1 of the proximal outer section 21 remains the same independently whether the distal outer section 22 is in the unexpanded or in the expanded state.

It is particularly noted that the inner and outer diameters in the region of the transition between the proximal outer section 21 and the distal outer section 22 are constant along the longitudinal direction in the expanded state of the distal outer section 22 and are continuously decreasing from the proximal to the distal outer section in the unexpanded state of the distal outer section. Thus, no abrupt changes or discontinuities of the inner and outer diameters are present in the transition in both the expanded and the unexpanded state of the distal outer section 22.

The coil 231 of the inner tubular element 23 can be formed from a wire made from e.g. metal or polymer. The wire can have a cross-sectional profile that is round, in particular circular, or rectangular, in particular flat. Alternatively, the inner tubular element 23 may be constructed from a laser-cut or patterned tube or from a flexible tube made from thermoplastic or composite.

The proximal end of the inner tubular element 23 is preferably connected to a handling means for the clinician to facilitate sliding of the inner tubular element 23 with respect to the outer sections 21, 22 of the catheter 2. This allows the tubular structure to be slid from the larger diameter D1 proximal outer section 21 into the smaller diameter D2 distal outer section 22 and, thus, causing expansion of the distal outer section 22, as shown in FIG. 1b. The presence of the inner tubular element 23 within the expanded distal outer section 22 adds an additional hoop strength to the distal outer section 22 rendering it more resistant to collapse when exposed to radial forces such as in the case of negative pressure or vacuum.

The mesh-like reinforcement element 222 of the distal outer section 22 is formed by a braided structure which can particularly be made from nitinol (NiTi). The outer hull 223 is preferably made from a polymer.

Figure 1C:
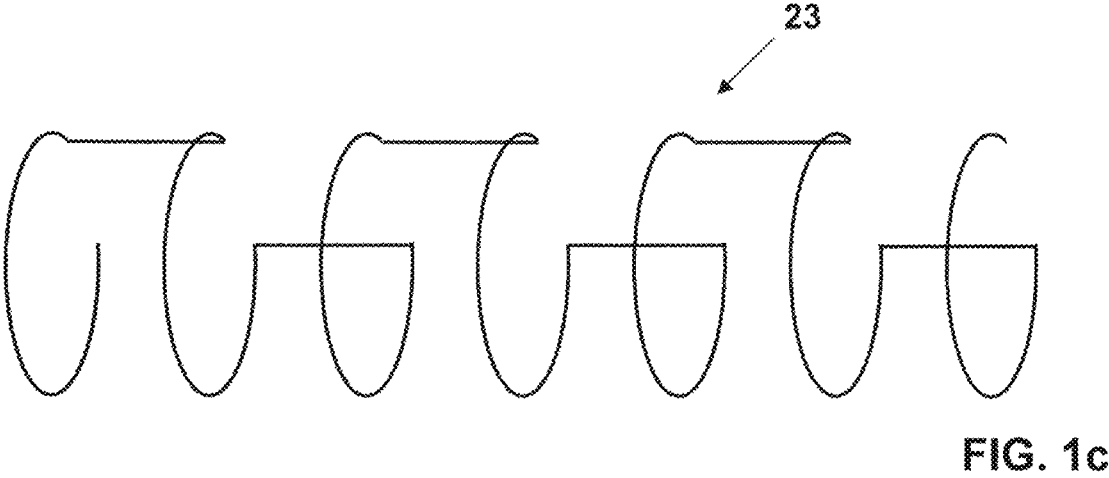
Figure 1D:
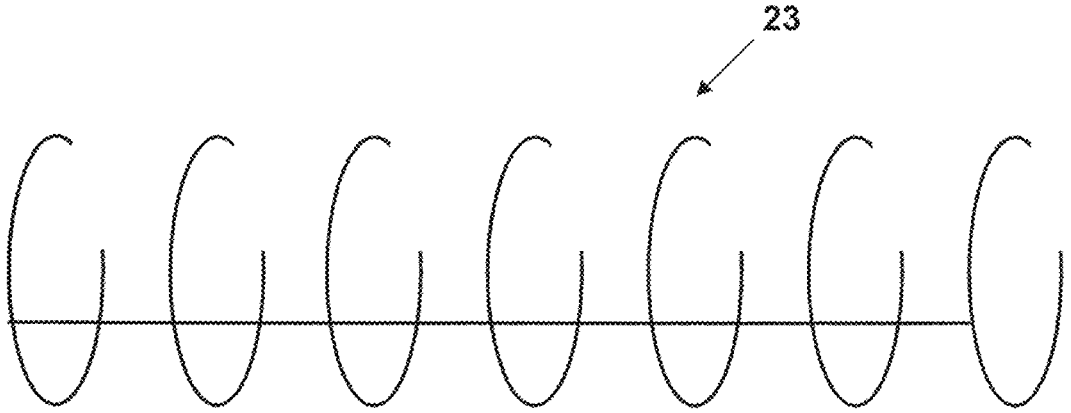
FIG. 1d shows another variant of an inner tubular element that can be used in combination with the catheter of FIG. 1a, FIG. 2a shows a side view of a catheter of an apparatus according to a second embodiment of the invention, with partially cut open outer hull, in the unexpanded state of the distal outer section.

FIGS. 1c and 1d show variants for the inner tubular element 23 of the embodiment of FIGS. 1a and 1b. Instead of being in the form of a coil 231, the inner tubular element 23 could also be in the form of a continuous wire forming rib-like structures, as shown in FIG. 1c. The rib-like structures formed by the wire extend in alternating circumferential directions and over at least a part of the circumference in each case. In the present embodiment, each of the rib-like structures has a rectangular shape. In other embodiments, the rib-like structures could of course also have other shapes, for example be rounded etc. A further variant of the inner tubular element 23 is shown in FIG. 1d. The inner tubular element 23 is here in the form of a plurality of C-shaped elements that are attached, in particular welded, to a longitudinally extending wire. In another variant, the C-shaped elements could also be circumferentially closed, i.e. be O-shaped. The variants of FIGS. 1c and 1d have the advantage that the inner tubular element 23 is radially compressible to a certain degree, which can lead to a smoother transition from the proximal outer section 21 to the distal outer section 22.

Figure 2A:
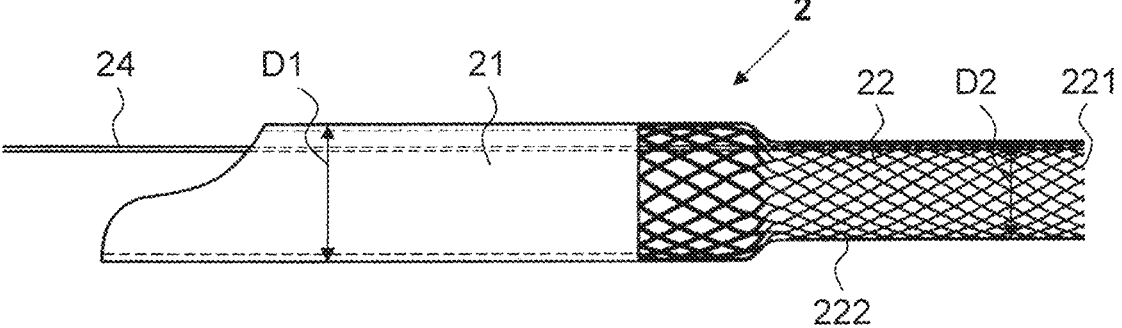
FIG. 2b shows the catheter of FIG. 2a, in the expanded state of the distal outer section.
Figure 2B:
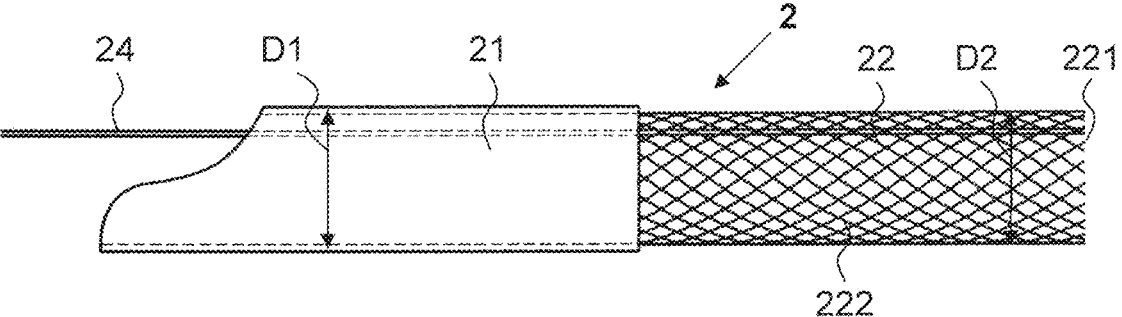

FIGS. 2a and 2b show an embodiment of an inventive catheter 2 which differs from the one of FIGS. 1a and 1b by not having an inner tubular element 23, but instead a pull element 24 as the actuation element for converting the distal outer section 22 from the unexpanded state as shown in FIG. 2a into the expanded state as shown in FIG. 2b. The pull element 24, which is here provided in the form of a pull thread, is attached to the distal end 221 of the distal outer section 22 and extends along the entire length of the catheter 2, such that it can be handled by the clinician during the intervention.

As long as not pulling force is applied to the pull element 24, the distal outer section 22 is in its unexpanded state as shown in FIG. 2a. If, however, a pulling force is applied to the pull element 24 by the clinician, the pull element 24 longitudinally compresses the distal outer section 22 against the proximal outer section 21. As a result of the longitudinal compression, the distal outer section 22 is radially expanded (FIG. 2b).

Figure 3A:
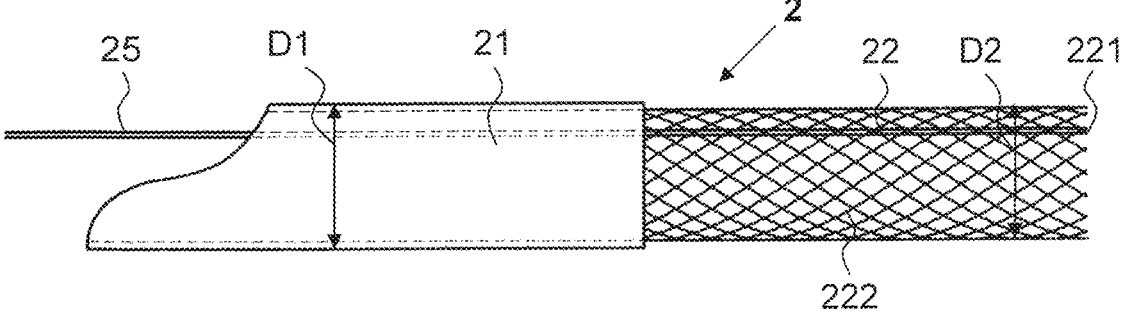
FIG. 3a shows a side view of a catheter of an apparatus according to a third embodiment of the invention, with partially cut open outer hull, in the expanded state of the distal outer section.
Figure 3B:
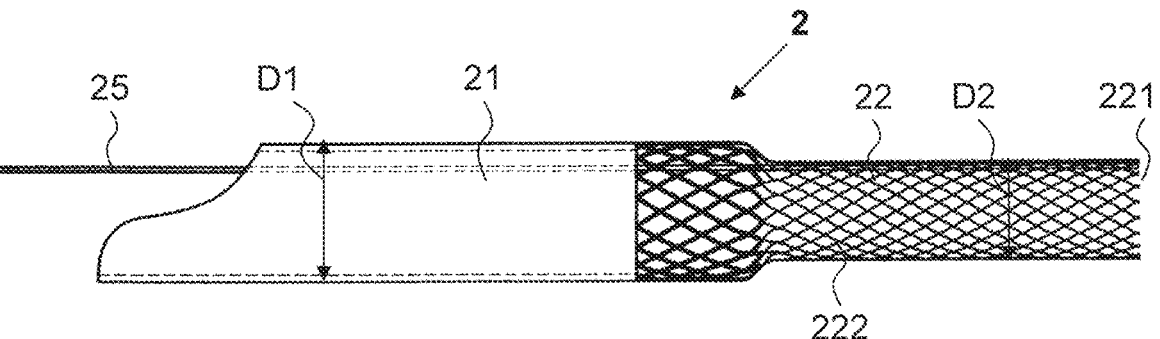
FIG. 3b shows the catheter of FIG. 3a, in the unexpanded state of the distal outer section.

In the embodiment of FIGS. 3a and 3b, a push element 25 instead of a pull element 24 is provided as the actuation element. The push element 25, which is here provided in the form of push thread, is attached to the distal end 221 of the distal outer section 22. In this embodiment, the reinforcement element 222, which is in the form of a braided structure, holds the distal outer section 22 in its expanded state, if no force is applied by the push element 25. Thus, in the relaxed state, the distal outer section 22 is expanded as shown in FIG. 3a. By applying a pushing force to the push element 25, the distal outer section 22 which is attached to the proximal outer section 21 is longitudinally stretched which causes a radial contraction of the reinforcement element 222 and thus of the proximal outer section 21.

Figure 4A:
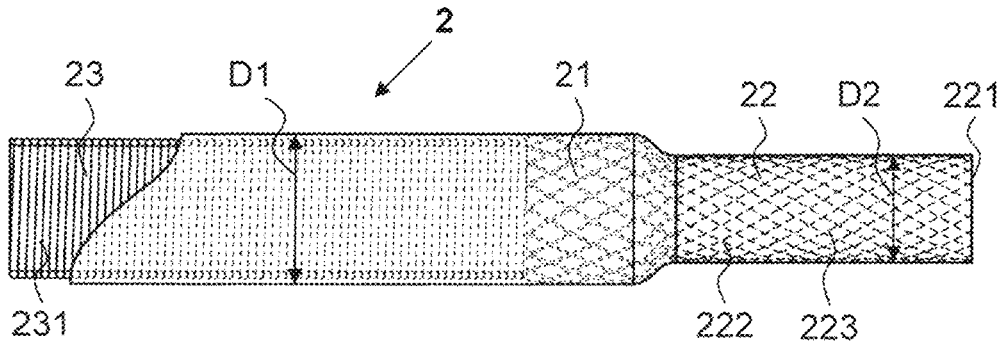
FIG. 4a shows a side view of a catheter of an apparatus according to a fourth embodiment of the invention, with partially cut open outer hull, in the unexpanded state of the distal outer section.
Figure 4B:
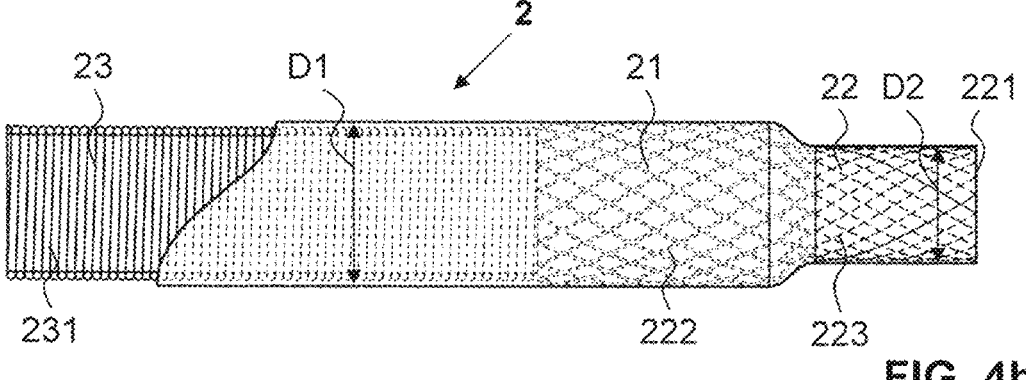
FIG. 4b shows the catheter of FIG. 4a, in a partially expanded state of the distal outer section.
Figure 4C:
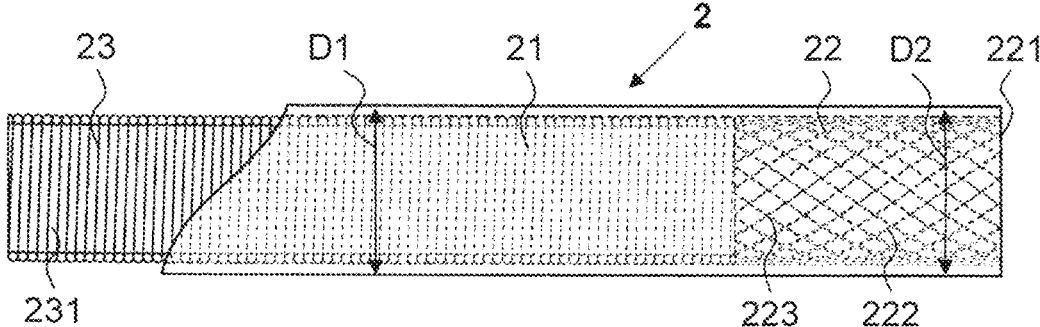
FIG. 4c shows the catheter of FIG. 4a, in the expanded state of the distal outer section.

In the embodiment of FIGS. 4a to 4c, a first distal end of the reinforcement element 222 is attached to the outer hull 223 and a second proximal end of the reinforcement element 222 is attached to the inner tubular element 23. Also in this embodiment, the reinforcement element 222 is formed by a braided structure. The outer hull 223 in this case preferably has a certain radial elasticity, but no or only a minor longitudinal elasticity.

In the relaxed state, the distal outer section 22 is unexpanded as shown in FIG. 4a. By distally moving forward the inner tubular element 23 relatively to the proximal and distal outer sections 21, 22, the reinforcement element 222 is longitudinally compressed and, as a result, radially expanded, as shown in FIG. 4b until the fully expanded state of the distal outer section is reached, as shown in FIG. 4c.

In an alternative embodiment, the inner tubular element 23 of the embodiment shown in FIGS. 4a to 4c is not attached to the proximal end of the reinforcement element 222, i.e. the braided structure, but only abuts thereto or to an element attached to the proximal end of the reinforcement element 222. This allows the catheter 2 to be navigated to the required location without the inner tubular element 23. The inner tubular element 23 can then be forwarded through the catheter 2 to expand the distal outer section 22, when the distal outer section 22 has reached the desired location within the body of the patient.

The embodiment of FIGS. 5a to 5c only differs from the one of FIGS. 4a to 4c by the inner tubular element 23 which is here in the form of a hypotube instead of a tightly wound coil.

Figure 6A:
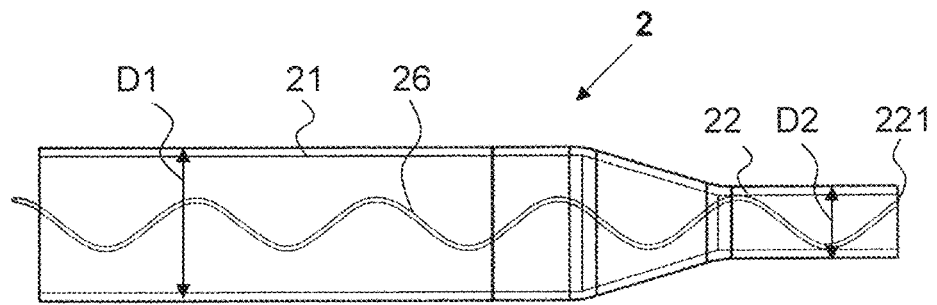
FIG. 6a shows a side view of a catheter of an apparatus according to a sixth embodiment of the invention, with an actuation element in the form of an inner coiled thread made visible, in the unexpanded state of the distal outer section.
Figure 6B:
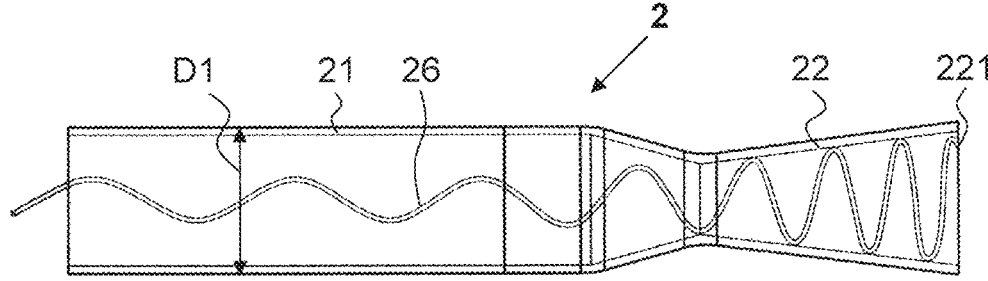
FIG. 6b shows the catheter of FIG. 6a, in a partially expanded state of the distal outer section.
Figure 6C:
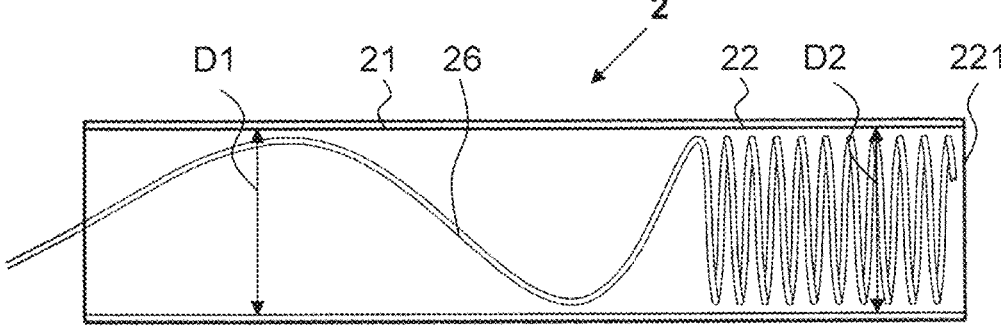
FIG. 6c shows the catheter of FIG. 6a, in the expanded state of the distal outer section.

FIGS. 6a to 6c show a further embodiment of the catheter 2. In this case, the distal outer section 22 is again formed by an elastic material which, in the relaxed state, gives the distal outer section 22 the unexpanded form as shown in FIG. 6a. In the present embodiment, a coiled thread 26 is arranged in the inner lumen of the catheter 2 and in particular of the distal outer section 22. The distal end of the coiled thread 26 is attached to the distal end 221 of the distal outer section 22. The coiled thread 26 is adapted to radially increase its outer diameter in the region of the distal outer section 22 when being longitudinally compressed by e.g. a clinician, as shown in FIG. 6b. In doing so, the coiled thread 26 radially expands the distal outer section 22 until the expanded state is reached (FIG. 6c).

The coiled thread 26 is preferably made from a memory-shape material, in particular a memory-shape alloy, such nitinol. Owing to the memory-shape material, the coiled thread 26 is preferably adapted to adopt a configuration as shown in FIG. 6c when being longitudinally compressed, with an increased radius and a larger number of windings being present in the region of the distal outer section 22.

Figures 7A, 7B, 8A, 8B:
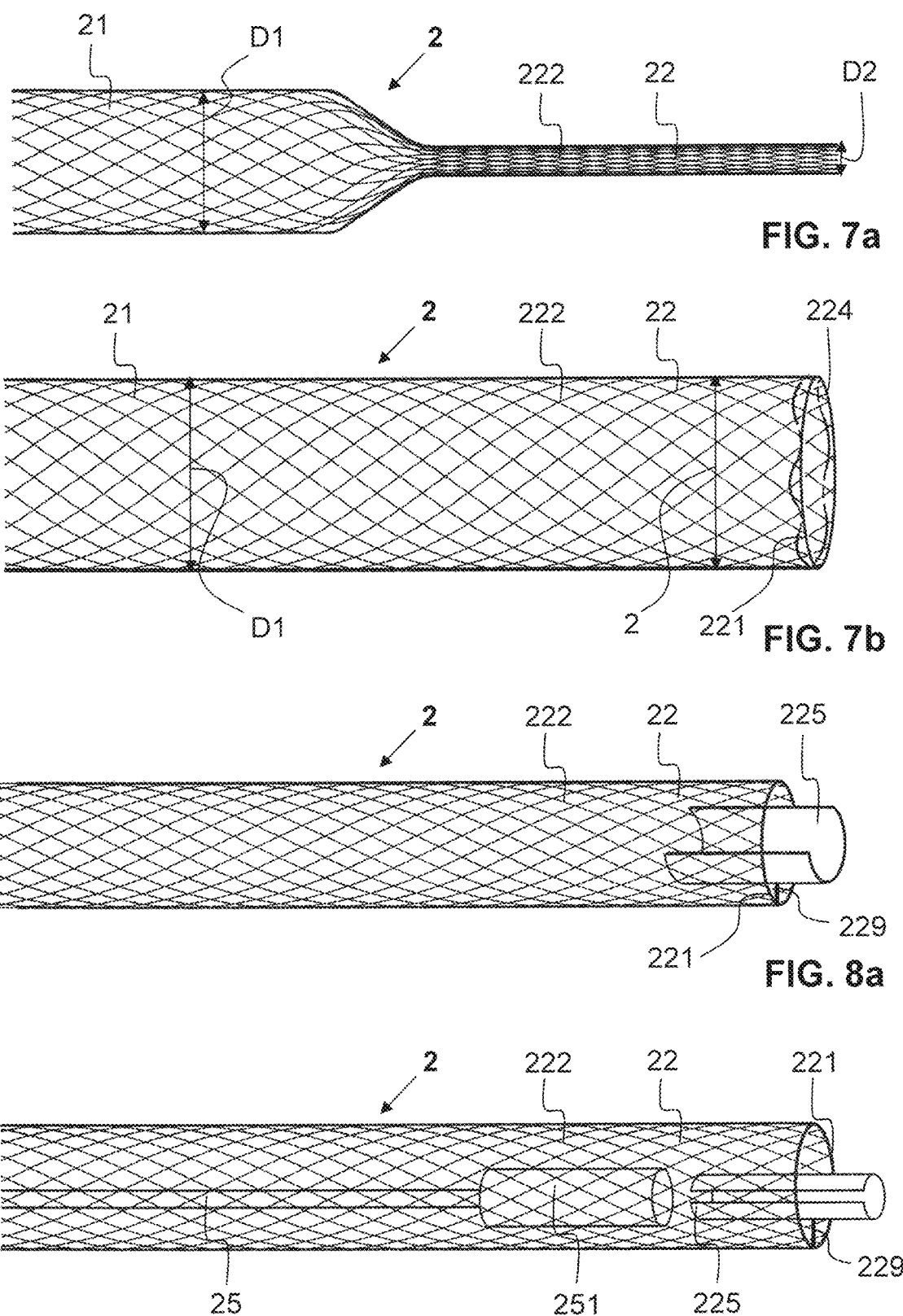
FIG. 7a shows a side view of a catheter of an apparatus according to an eighth embodiment of the invention, in the unexpanded state of the distal outer section.
FIG. 7b shows the catheter of FIG. 7a, in the expanded state of the distal outer section.
FIG. 8a shows a side view of a catheter of an apparatus according to a ninth embodiment of the invention, in the relaxed, expanded state of the distal outer section.
FIG. 8b shows the catheter of FIG. 8a, in the expanded state of the distal outer section.

FIGS. 7a and 7b show a further embodiment of the catheter 2, wherein the unexpanded state of the distal outer section 22 is shown in FIG. 7a and the expanded state in FIG. 7b. In the expanded state, the outer diameter D2 of the distal outer section 22 is the same as the outer diameter D1 of the proximal outer section 21. In the unexpanded state of FIG. 7a, however, the diameter D2 of the distal outer section 22 is smaller by a multiple than the diameter D1 of the proximal outer section 21.

In its relaxed state, the distal outer section 22 can be in either the unexpanded state as shown in FIG. 7a or in the expanded state as shown in FIG. 7b.

The catheter 2 of FIGS. 7a and 7b has a reinforcement element 222 in the form of a braided structure that is provided along the entire distal outer section 22 and, in the current embodiment, along at least the distal end part of the proximal outer section 21. The reinforcement element 222 ensures not only the required flexibility for the distal outer section 22 to be navigated through the vasculature of the patient, but also enhances the mechanical rigidity and resistance of the catheter 2 with regard to torque and column strength. In the expanded state of the distal outer section 22, the reinforcement element 222 is adapted to resist the vacuum which is applied within the inner lumen of the catheter 2 and, thus, to prevent the catheter 2 from collapsing. Furthermore, the reinforcement element 222 is adapted to radially expand, when being longitudinally compressed, and/or to radially contract, when being longitudinally stretched. Thus, the reinforcement element 222 is adapted to effect the change of the unexpanded state into the expanded state and vice versa, of the distal outer section 22. For this purpose, an actuating element in the form of a push or pull element (not shown in FIGS. 7a, b) can be attached, in particular releasably attached, to the distal end 221 or to the proximal end of the distal outer section 22.

The distal end 221 of the distal outer section 22 can be reinforced by means of a circumferential reinforcing wire 224, as shown in FIG. 7*b*. The push or pull element can be attached to the reinforcing wire 224.

FIGS. 8*a* and 8*b* show an embodiment of a catheter 2 having a design as the embodiment of FIGS. 7*a* and 7*b*, but additionally comprising a semi-cylindrical spring structure 225 which is fixedly attached to the distal end 221 of the distal outer section 22 by means of an attachment element 229. The semi-cylindrical spring structure 225 extends co-axially along the longitudinal center axis of the catheter 2 and can be radially compressed by rolling up the structure more. In the compressed state, as shown in FIG. 8*b*, the semi-cylindrical spring structure 225 adopts an almost fully cylindrical shape with a through-slit extending along the entire length of the structure.

In its radially compressed state, the semi-cylindrical spring structure 225 can be received by a receiver cylinder 251 which forms the distal end of a push element 25. The push element 25 can for example be a push tube or a push thread. The receiver cylinder 251 is closed towards the proximal direction by an end surface. When being received by the receiver cylinder 251, the semi-cylindrical spring structure 225 proximally abuts this end surface. Thus, the semi-cylindrical spring structure 225 and therewith the distal end 221 of the distal outer section 22 can by pushed distally by the push element 25, in order to longitudinally stretch the distal outer section 22. Due to the reinforcement element 222, i.e. the braided structure, the distal outer section 22 is radially contracted, when being longitudinally stretched, in order to adopt its unexpanded state.

In use, the catheter 2 of FIGS. 8*a* and 8*b* is inserted into and navigated through the patient's circulation with the push element 25 extending along the entire inner lumen of the catheter 2 and with the semi-cylindrical spring structure 225 being received within the receiver cylinder 251, in order to longitudinally stretch the distal outer section 22 and to hold it in its unexpanded state. After having reached the desired position in the circulatory system, the push element 25 can be partially retracted from the catheter 2, in order to bring the distal outer section in its expanded state for clot aspiration. The retraction can be such that the semi-cylindrical spring structure 225 remains within the receiver cylinder 251, in order to enable a longitudinal stretching of the distal outer section 22 later on. Alternatively, the push element 25 can be retracted completely from the catheter 2, in order to start the aspiration process, possibly with the help of a clot-retriever that is forwarded through the catheter 2 for the clot retrieval.

Figure 9A:
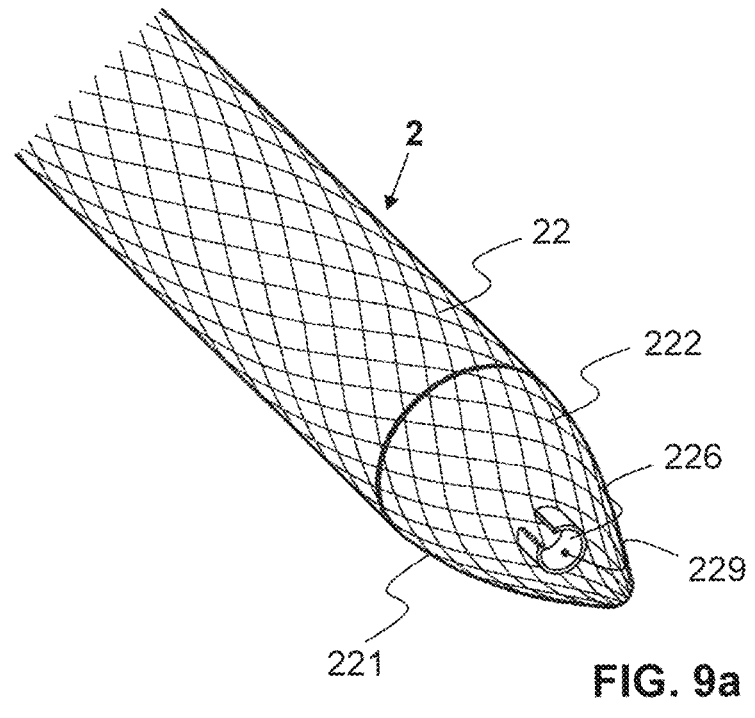
FIG. 9a shows a perspective view of a catheter of an apparatus according to a tenth embodiment of the invention, in the relaxed, expanded state of the distal outer section.
Figure 9B:
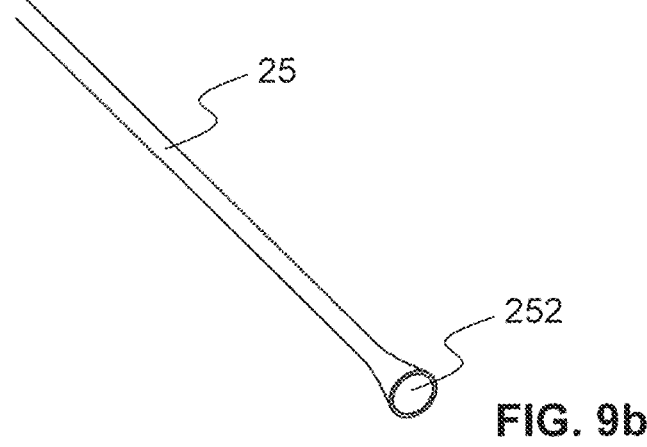
Figure 9C:
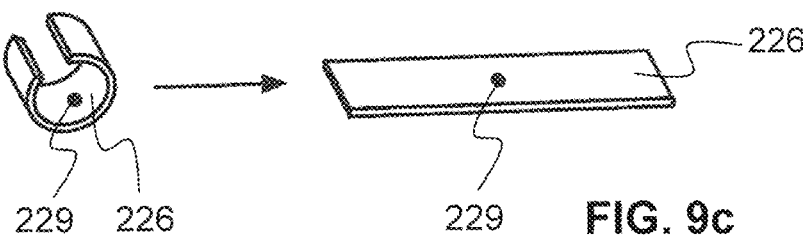
FIG. 9c shows a perspective view of the spring clip which is attached to the catheter of FIG. 9a and serves to hold the push element of FIG. 9b, in a rolled up configuration as used in FIG. 9a and in a flat configuration.

FIGS. 9*a*-9*c* show an embodiment of a catheter 2 with a pointed distal end 221. In the relaxed state, the distal outer section 22 of the catheter 2 is in its expanded state, as shown in FIG. 9*a*. In order to bring and hold the outer distal section 22 in its unexpanded state for navigating the catheter 2 through the circulatory system of the patient, a push element 25 with a widened end 252 is provided. The push element 25, which can particularly be a push tube, is guided all along through the catheter 2 and the widened end 252 is engaged by a spring clip 26 that is attached to the distal end 221 of the distal outer section 22 by means of an attachment element 229. By further pushing the push element 25 distally into the catheter 2, the distal outer section 22 is longitudinally stretched due to the attachment of the widened end 252 to the spring clip 226. As a result and due to the reinforcement element 222 in the form of a braided structure, the distal outer section 22 is radially contracted. The spring clip 226 can be formed by rolling a simple rectangular plate, as shown in FIG. 9*c*.

In a different embodiment, the distal outer section 22 of the catheter 2 of FIG. 9*a* could be in its unexpanded state, when relaxed. The actuation element for bringing the distal outer section 22 into the expanded state could then be a pull element instead of a push element. By pulling the pull element proximally, the distal outer section 22 would be longitudinally compressed and as a result radially expanded due to the attachment of the pull element to the spring clip 226 and due to the reinforcement element 222.

Figure 10A:
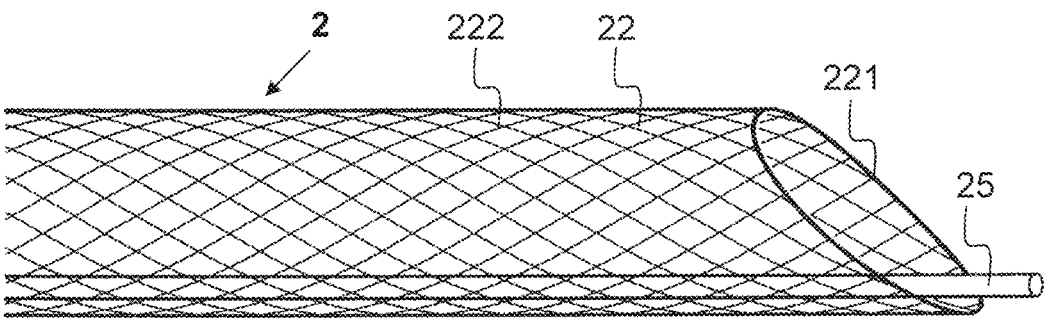
FIG. 10a shows a side view of a catheter with inserted push element of an apparatus according to an eleventh embodiment of the invention, in the relaxed, expanded state of the distal outer section.
Figure 10B:
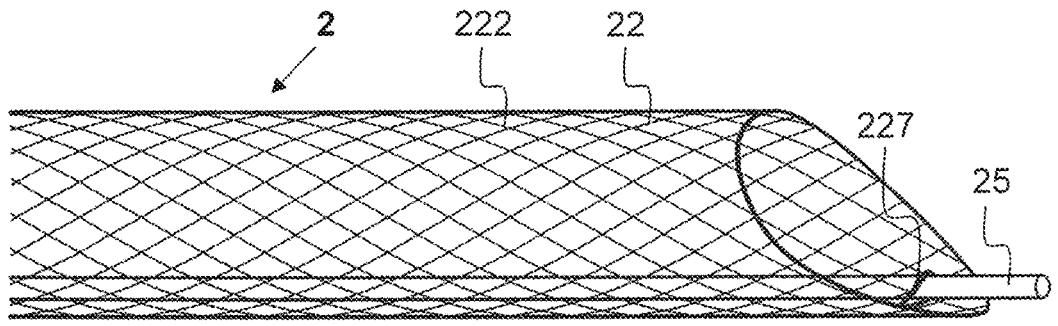
FIG. 10b shows the catheter of FIG. 10a, with the push element being releasably attached to the catheter by means of an elastic loop.
Figure 10C:
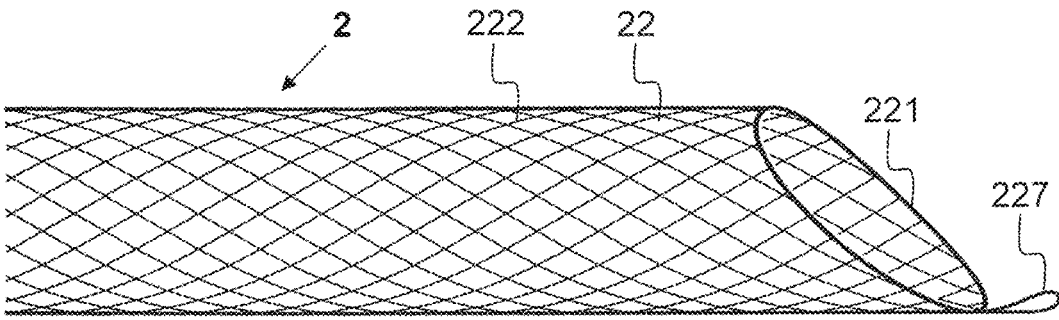
FIG. 10c shows the catheter of FIG. 10a, with the elastic loop attached to the distal end of the catheter.

FIGS. 10*a* to 10*c* show an embodiment with a catheter 2 having a pointed distal outer section 22. Similarly as in the embodiment of FIGS. 9*a*-9*c*, the catheter 2 also comprises a reinforcement element 222 in the form of a braided structure which holds the distal outer section 22 in its expanded state, when relaxed. In order to radially contract the distal outer section 22, a push element 25, e.g. a push thread or a push tube, is guided all along through the catheter 2 and is attached to the distal end 221 of the distal outer section 22 by means of an elastic loop 227. The elastic loop 227 is fixedly attached to the distal end 221 of the catheter 2 and holds the push element 25 by means of friction. A part of the outer surface of the push element 25 can comprise a friction-enhancing coating, in order to improve the attachment of the push element 25 to the loop 227. If the friction-enhancing coating is only provided on one side of the push element 25, the push element 25 can be rotated, in order to release the attachment. The loop 227 can be interwoven with the reinforcement element 222, i.e. the braided structure.

Figure 11:
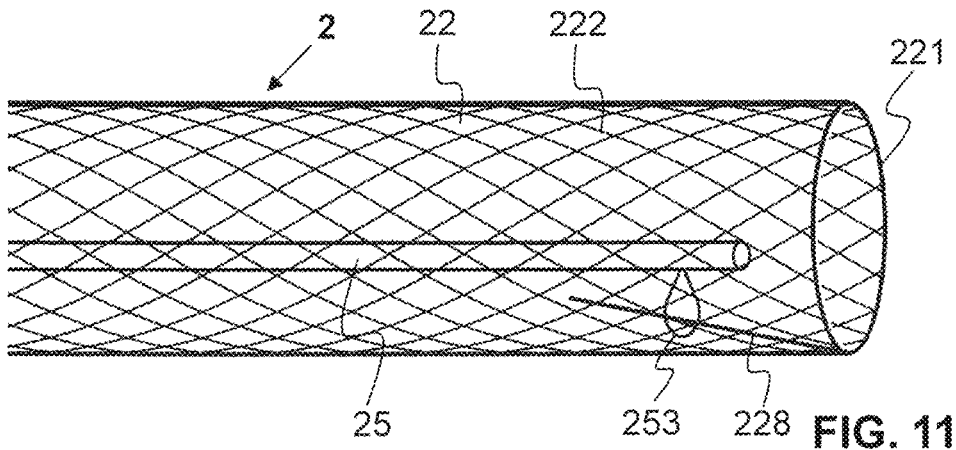
FIG. 11 shows a side view of a catheter with inserted push element of an apparatus according to a twelfth embodiment of the invention, in the relaxed, expanded state of the distal outer section.

FIG. 11 shows a further option for releasably attaching the push element 25 to the distal end 21 of the catheter 2. A loop 253 is here attached to the distal end of the push element 25. For radially contracting the distal outer section 22, the push element 25 is such inserted into the catheter 2, that the loop 253 is engaged by a hooked element 228 which is attached to the distal end 221 of the catheter 2. As in the case of FIG. 11, the hooked element 228 can be in the form of a simple stiff wire that extends proximally from the distal end 221 into the inner lumen of the catheter 2. By engaging the loop 253 with the hooked element 228 and further pushing the push element 25 along the distal direction relative to the catheter 2, the distal outer section is longitudinally stretched and, as a result, radially contracted due to the braided reinforcement element 222.

Figure 12A:
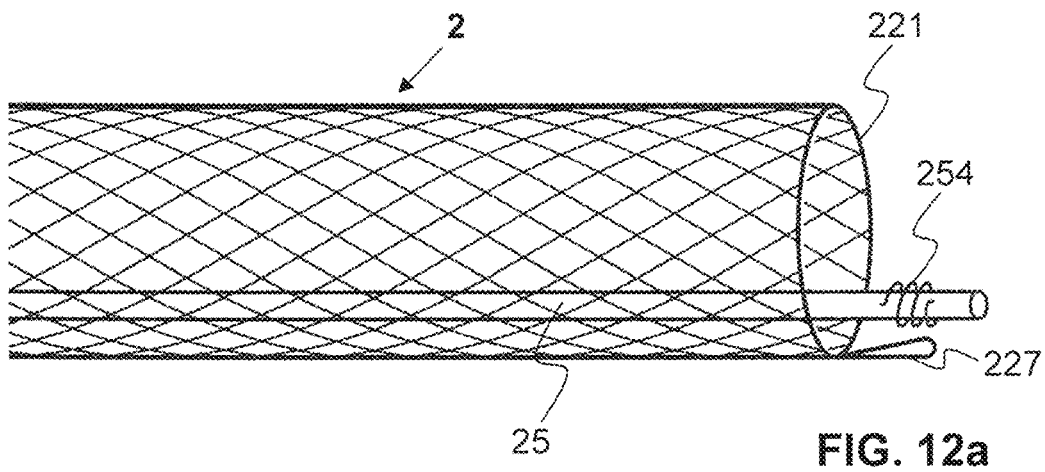
FIG. 12a shows a side view of a catheter with inserted push element of an apparatus according to a thirteenth embodiment of the invention, in the relaxed, expanded state of the distal outer section.
Figure 12B:
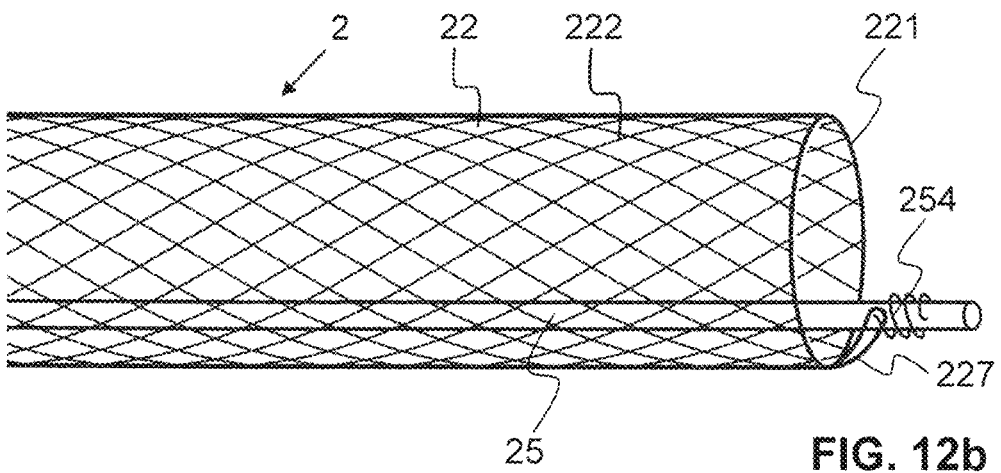
FIG. 12b shows the catheter of FIG. 12a, with the push element being releasably attached to the catheter by means of a spiral coil and an elastic loop.

Yet another option for releasably attaching the push element 25 to the distal end 221 of the catheter 2 is shown in FIGS. 12*a* and 12*b*. In this embodiment, a coil spring 254 is attached with a first end to the distal end part of the push element 25. From its attached first end, the coil spring 254 is wound around the push element 25 along the proximal direction. The second end is not attached, but slightly protrudes from the push element 25, such that it can easily be inserted into a loop 227 which is attached to the distal end 221 of the catheter 2. By rotating the push element 25, the loop 227 can be further screwed into the coil spring 254, in order to improve the attachment in such a way, that the distal end 221 of the catheter can be moved distally and proximally by means of the push element 25. For releasing the push element 25 from the distal end 221, the push element 25 can be rotated in the counter-direction.

Figures 13A, 13B, 14A, 14B:
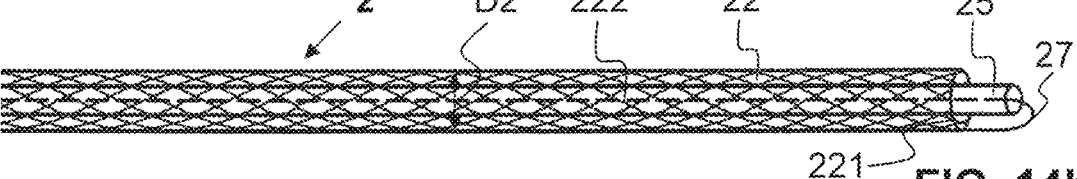
FIG. 13a shows a side view of a catheter of an apparatus according to a fourteenth embodiment of the invention, in the relaxed, expanded state of the distal outer section, with a loop being attached to the distal end of the catheter.
FIG. 13b shows the catheter of FIG. 13a, with a push element being inserted into the catheter in such a way that it is releasably attached to the loop and exerts a pulling force, in order to bring the distal outer section into its unexpanded state.
FIG. 14a shows a side view of a catheter of an apparatus according to a fifteenth embodiment of the invention, in the relaxed, expanded state of the distal outer section, with a push element inserted into the catheter and releasably connected thereto via a trailing wire.
FIG. 14b shows the catheter of FIG. 14a, with the push element being locked to the trailing wire in such a way that it exerts a pulling force onto the distal end of the catheter, in order to bring the distal outer section into its unexpanded state.

The embodiment shown in FIGS. 13*a* and 13*b* corresponds to the one of FIGS. 10*a*-10*c*, except that the distal end 221 is not pointed here and that the distal outer section 22 does not have a cylindrical shape in the unexpanded state. Instead, as shown in FIG. 13*b*, the distal end part of the distal outer section 22 is contracted to adopt a hemisphere-like shape in the unexpanded state. The loop 227 is formed by a continuation of the reinforcing wire 224 for this purpose.

A particularly preferred embodiment is shown in FIGS. 14*a* and *b*. FIG. 14*a* shows the distal outer section 22 of the catheter 2 in the relaxed expanded state. The distal outer section 22 is held in this expanded state by the braided reinforcement element 222. For radially contracting the distal outer section 22, a hollow push element 25 in the form of a push tube is inserted lengthwise into the catheter 2 in such a way that a trailing wire 27 extends through the push tube along the entire length thereof. The trailing wire 27 is attached to the distal end 221 of the catheter 2. It can be formed by a continuation of the reinforcing wire 224. The push element 25 protrudes from the proximal end of the catheter 2. Likewise, the trailing wire 27 protrudes from the proximal end of the push element 25, such that the physician can operate both the push element 25 and the trailing wire. By drawing the trailing wire 27 proximally relative to the catheter 2, such that it is taut, and holding the trailing wire 27 in this position, while at the same time forwarding the push element 25 distally at least up to the attachment point of the trailing wire 27 to the distal end 221 of the catheter 2, the trailing wire 27 and the push tube 25 can be locked to each other. If the push tube 25 is then further moved distally relative to the catheter 2, the distal outer section 22 is longitudinally stretched and, due to the reinforcement element 222, radially contracted (FIG. 14*b*). The locking of the trailing wire 27 and the push tube 25 can be released by releasing the trailing wire 27 with respect to the catheter 2.

For facilitating the handling for the physician, an operating instrument can be provided in all of the above-mentioned embodiments, in which the proximal ends of the catheter 2, of the push element 25 and, if provided, of the trailing wire 27 are arranged in such a way, that manipulations as explained above for radially contracting and/or expanding the distal outer section 22 are possible.

In all of the above-mentioned embodiments that comprise a braided structure, any other reinforcement element could be provided for the same purpose instead of the braided structure, such as e.g. a reinforcement element in the form of one or several helically wounded wires or in the form of interwoven filaments. Further possible variants for the at least one reinforcement element are shown in FIGS. 15 to 23.

FIG. 15 shows a reinforcement element 222 in the form of a knitted structure. With a knitted structure, a comparatively pronounced radial expansion of contraction can be achieved even with small longitudinal changes of the structure.

FIGS. 16 and 17 show two variants of possible knitting patterns that can be used in a knitted structure as the one shown in FIG. 15. By using the weft knit (FIG. 16) or the warp knit (FIG. 17), the directional elasticity of the knitted structure, i.e. the reinforcement element 222, can be controlled in such a way that a certain elasticity is provided in the radial direction, but no or only a reduced elasticity in the longitudinal direction.

Another alternative variant for the reinforcement element 222 is a crochet structure as shown in FIG. 18. Similar as with a knitted structure, a directional elasticity can be provided with a crochet structure in such a way that the elasticity of the structure is much more pronounced in the radial direction, than in the longitudinal direction.

Figure 19:
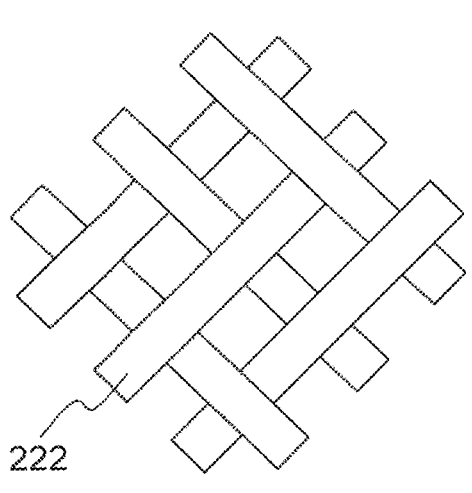
FIG. 19 shows a biaxial braid of a braided reinforcement element for a catheter of an inventive apparatus.
Figure 20:
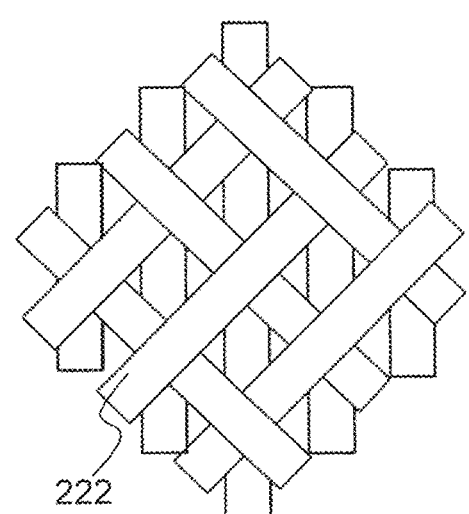
FIG. 20 shows a triaxial braid of a braided reinforcement element for a catheter of an inventive apparatus.

Further alternative variants for the reinforcement element 222 are shown in FIGS. 19 and 20 in the form of a biaxial braid (FIG. 19) and a triaxial braid (FIG. 20). In the biaxial braid, filaments are arranged in two different directions. In the present case of FIG. 19, the angle angle between the two filament directions is approximately 90°. Such a braid is radially expanded, when being longitudinal shortened. When another set of filaments is oriented in a third direction during braiding a triaxial braid results, as the one shown in FIG. 20. The third set of filaments can for example be used to limit the longitudinal movement in response to radial expansion and contraction.

Figure 21A:
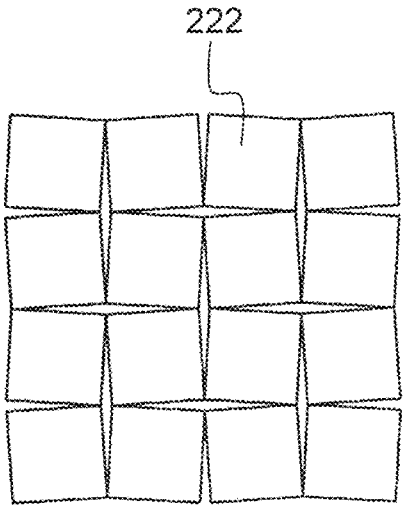
FIG. 21a shows an auxetic structure for forming a reinforcement element of a catheter of an inventive apparatus, in the contracted state.
Figure 21B:
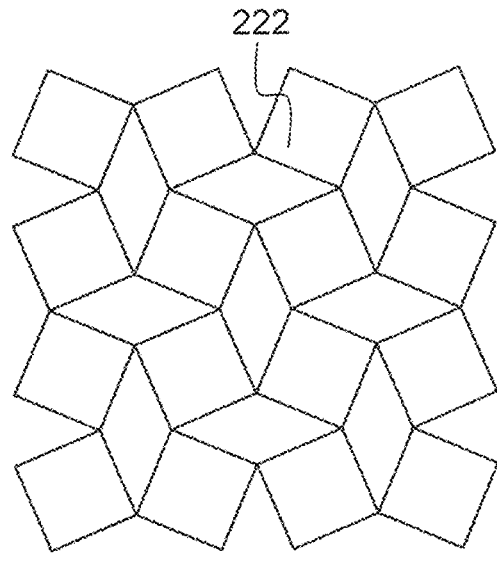
FIG. 21b shows the auxetic structure of FIG. 21a in the expanded state.

FIGS. 21*a* and 21*b* show a further variant of a reinforcement element 222, which is here formed by an auxetic structure or material. With an auxetic structure or material, it is possible to provide a reinforcement element 222 for the distal outer section 22, that is radially expanded, when being longitudinally stretched (FIG. 21*b*) or that is radially contracted, when being longitudinally compressed (FIG. 21*a*). Such a structure having a negative Poisson ratio can be obtained by means of a specific cutting pattern, e.g. as the one shown in FIGS. 21*a, b*.

Figure 22:
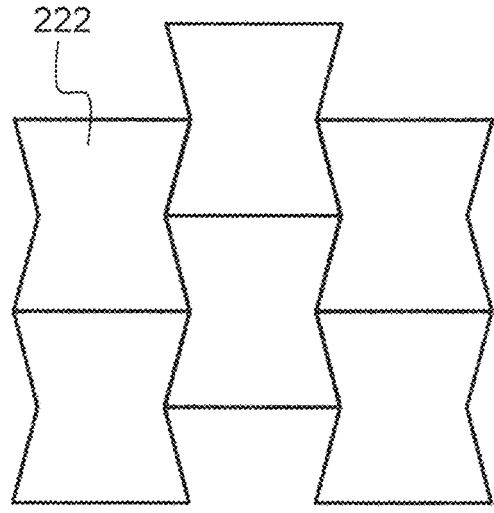
FIG. 22 shows a cutting pattern for providing another auxetic structure for forming a reinforcement element for a catheter of an inventive apparatus.
Figure 23:
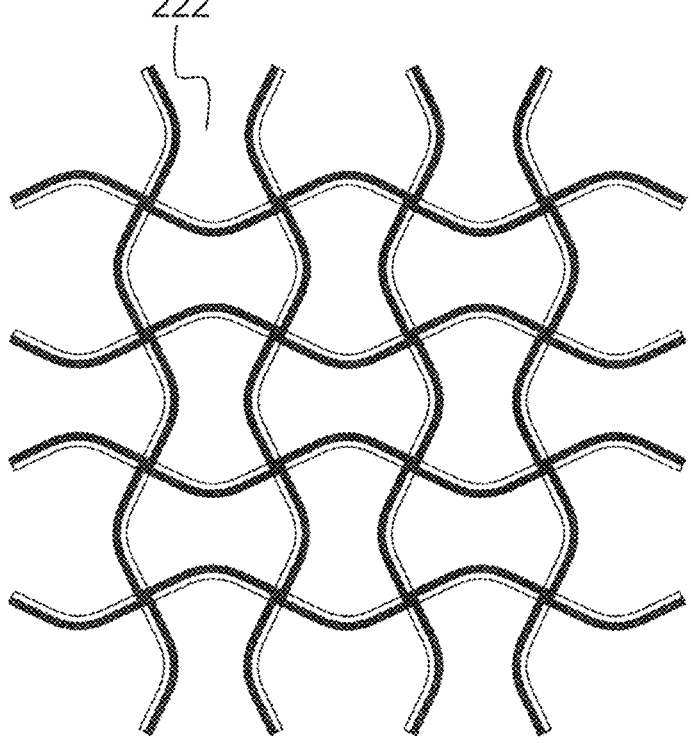
FIG. 23 shows a cutting pattern for providing yet another auxetic structure for forming a reinforcement element for a catheter of an inventive apparatus.

FIGS. 22 and 23 show two further types of cutting patterns that could be used to provide an auxetic structure, in order to form the reinforcement element 222. The patterns can for example be cut from a plastic or metallic tube and are known as re-entrant auxetic patterns.

In FIGS. 24*a* to 24*e* and 25*a* to 25*f*, the method steps for retrieval of a clot C from the intracranial vessels and from the circulatory system CS of a patient are shown in a larger scale (FIGS. 25*a* to 25*f*) and in more detail (FIGS. 24*a* to 24*e*). In the example of FIGS. 24*a* to 24*e* and 25*a* to 25*f*, the clot removal is achieved by means of aspiration and by means of a clot-retriever 3 that engages with the clot C. In other situations, however, the use of the clot-retriever might not be necessary and the clot could be removed by means of aspiration into to the catheter only.

Figures 24A, 24B, 24C, 24D, 24E:
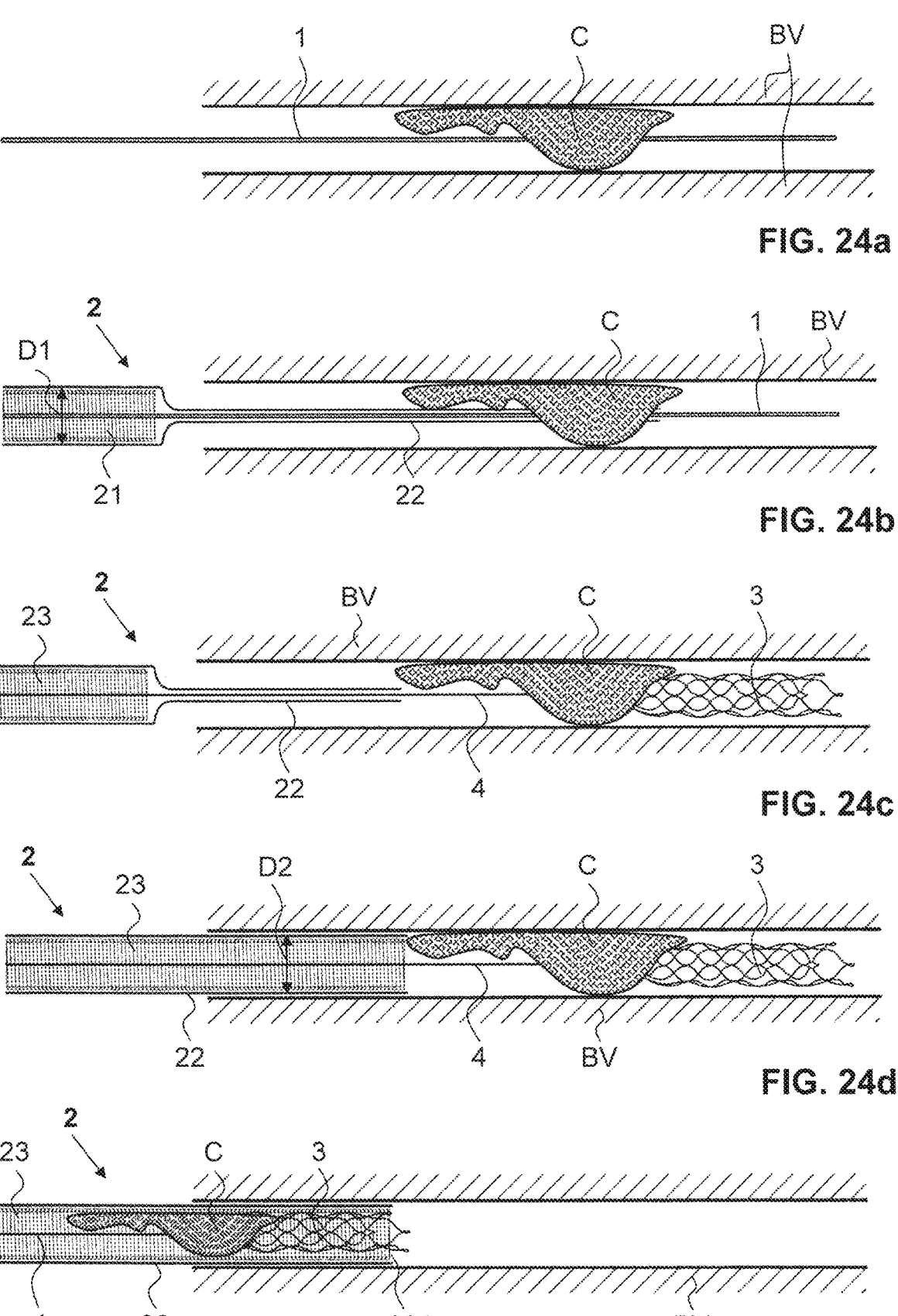
FIG. 24a shows a first step in the treatment of ischemic stroke by means of the apparatus as shown in FIGS. 1a and 1b, with the guide wire extending through a clot.
FIG. 24b shows a second step in the treatment of ischemic stroke by means of the apparatus as shown in FIGS. 1a and 1b, with the guide wire and the distal outer section of the catheter, in its unexpanded state, extending through the clot.
FIG. 24c shows a third step in the treatment of ischemic stroke by means of the apparatus as shown in FIGS. 1a and 1b, with the catheter, in a partially expanded state, partly retracted and with the clot-retriever deployed and engaged with the clot.
FIG. 24d shows a fourth step in the treatment of ischemic stroke by means of the apparatus as shown in FIGS. 1a and 1b, with the catheter, in its expanded state, and with the clot-retriever still engaged with the clot.
FIG. 24e shows a fifth step in the treatment of ischemic stroke by means of the apparatus as shown in FIGS. 1a and 1b, with the clot-retriever and the clot received in the expanded catheter, which is being retracted from the blood vessel.
Figure 25A:
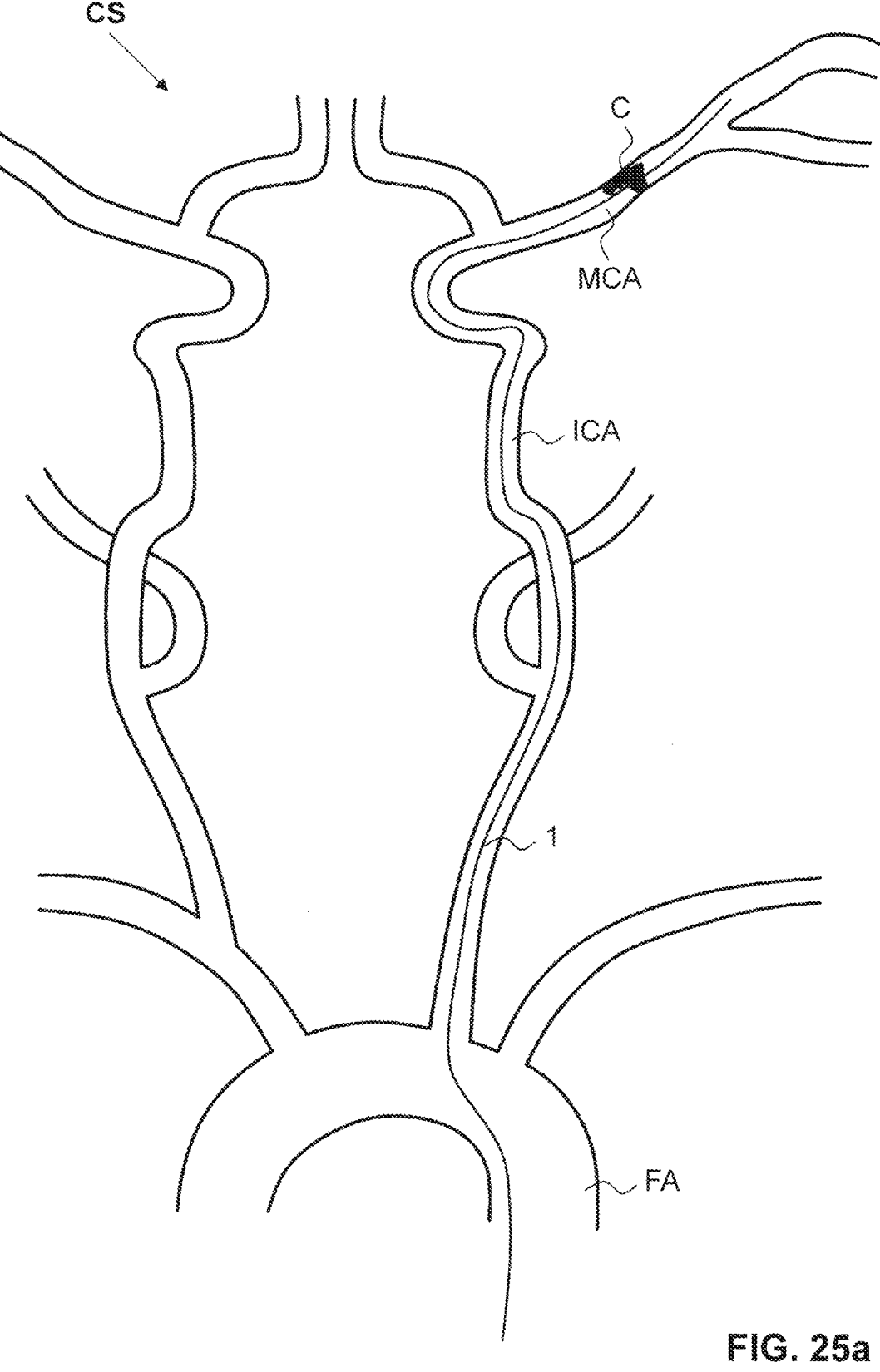
FIG. 25a schematically shows the insertion of a guide wire into the circulatory system of a patient for the treatment of ischemic stroke.

FIGS. 24*a* and 25*a* schematically illustrate the insertion and positioning of a guide wire 1 in the circulatory system CS of an animal or, as in the situation shown, of a human patient. It can particularly be seen in FIG. 25*a*, how the guide wire 1 is inserted in the region of the femoral artery FA into the circulatory system of the patient. From the point of insertion in the femoral artery FA, the guide wire 1 is forwarded through the aorta and into the internal carotid artery ICA and the middle cerebral artery MCA to the location of the clot C. The location of the clot C has been identified beforehand by means of X-ray computed tomography for example. Navigation of the guide wire 1 through the circulatory system CS is carried out according to state-of-the-art methods. The guide wire 1 can for example comprise fluoroscopic markers for this purpose. The guide wire 1 is navigated to the target position in such a way, that it extends along the blood vessel BV and through the clot C along of its longitudinal extension.

Figure 25B:
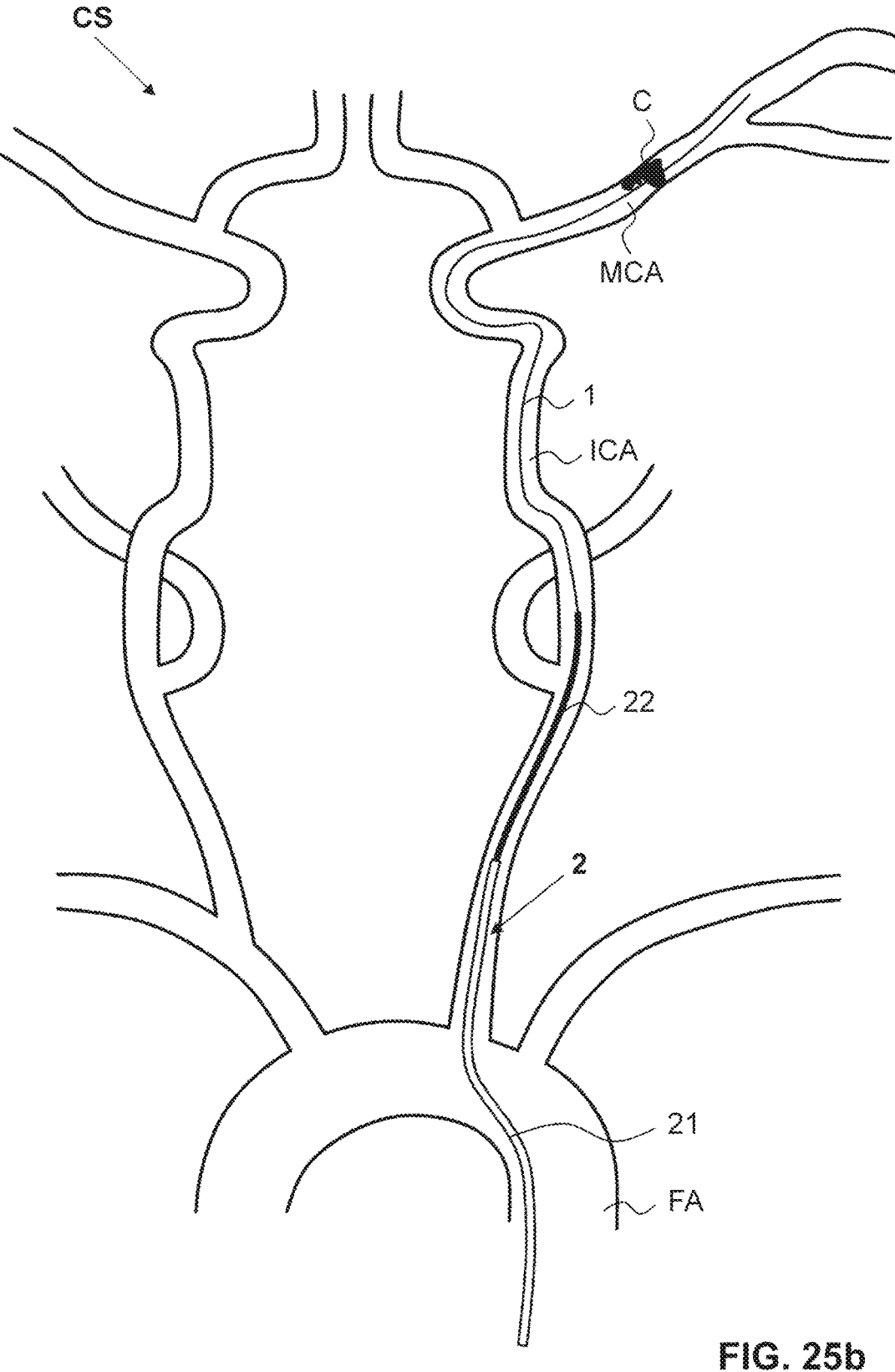
FIG. 25b schematically shows the partial insertion of an inventive catheter into the circulatory system along the guide wire of FIG. 25a, with the distal outer section of the catheter in unexpanded state.
Figure 25C:
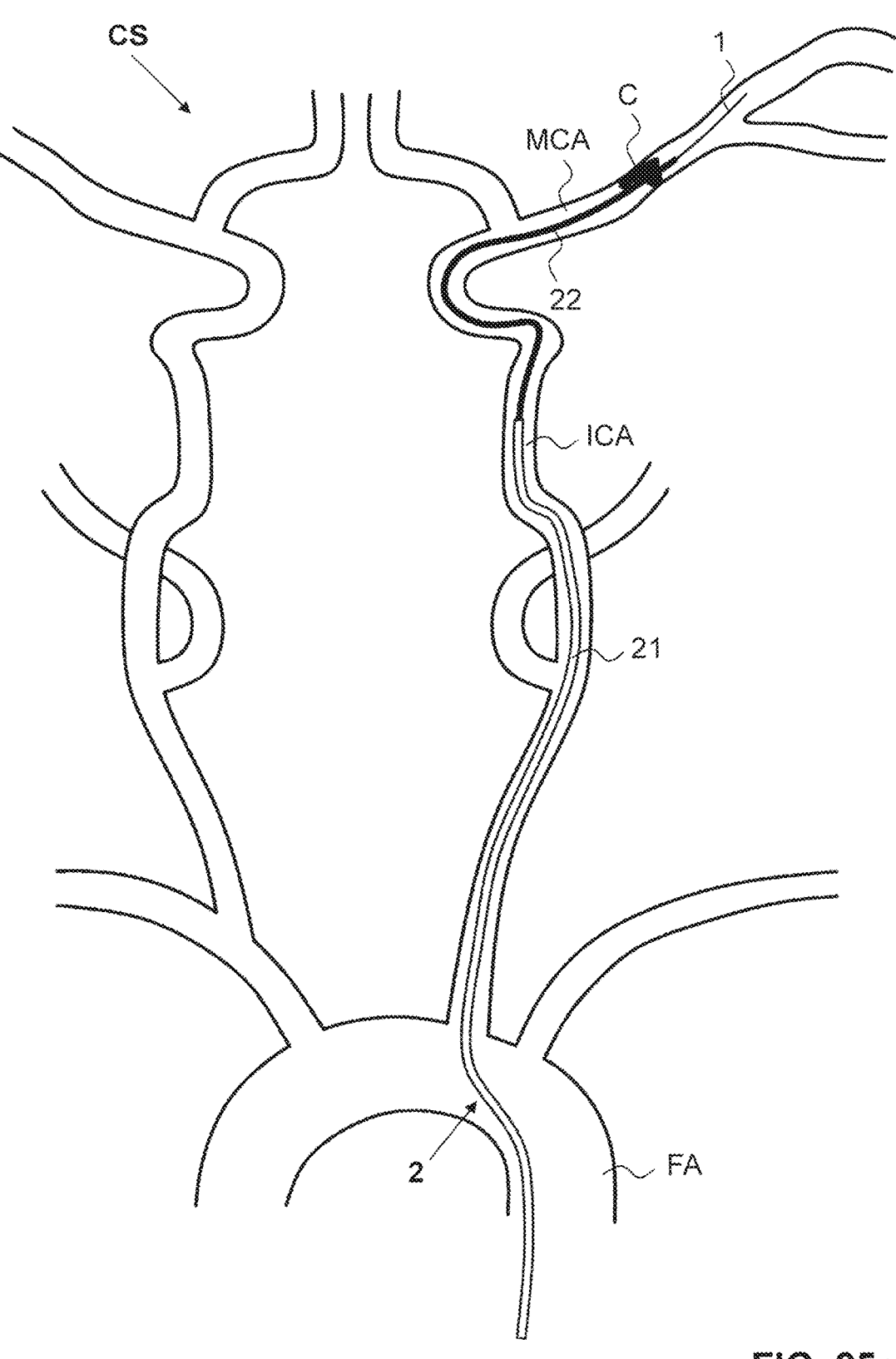
FIG. 25c schematically shows the catheter of FIG. 25b advanced further into the vasculature, such as to extend, with the unexpanded distal outer section, through a clot in the internal carotid artery.

In the next step shown in FIG. 25*b*, the catheter 2 is inserted and forwarded with the aid of the pre-positioned guide wire 1, in order to be positioned such that the distal outer section 22 of the catheter 2 extends through the clot C (FIGS. 24*b* and 25*c*).

The guide wire 1 is then retracted and replaced by a delivery wire 4. The delivery wire 4 has a distal end to which a clot-retriever 3 is attached. The clot-retriever 3 is adapted to engage with the clot C, in order to remove the clot C from the circulatory system and preferably has the form of stent-retriever as known by the skilled person. The clot-retriever 3 can, however, also have other forms and particularly comprise a plurality of clot engaging elements as disclosed in the yet unpublished European patent application EP 19 167 604.8 of the same applicant.

Figure 25D:
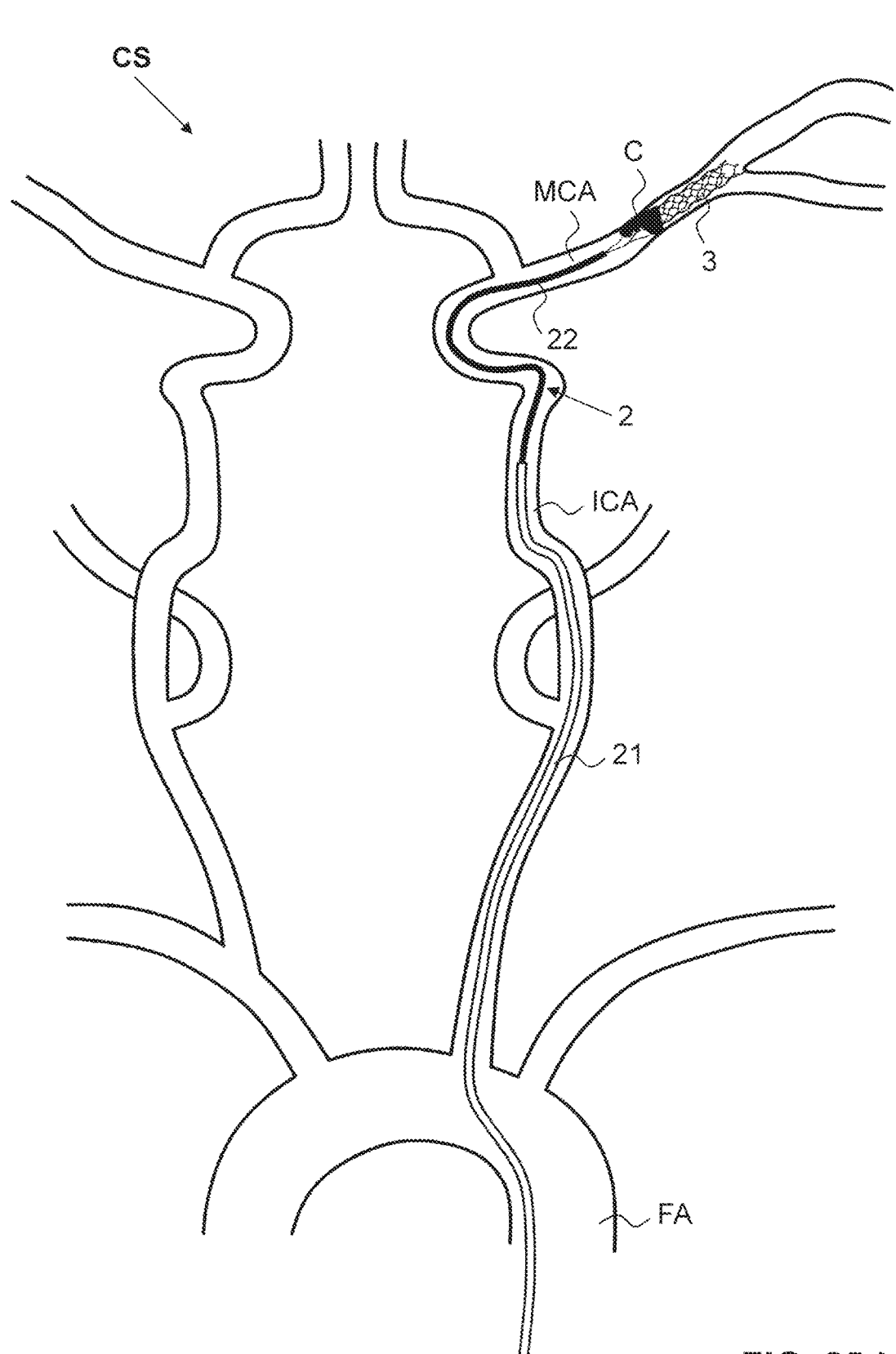
FIG. 25d schematically shows the catheter of FIGS. 25b and 25c, in unexpanded state and partly retracted, in order to deploy the clot-retriever which is engaged with the clot.

In the next step, the catheter 2 is partially retracted, in order to deploy the clot-retriever 3 which engages with the clot C (FIGS. 24c and 25d). Alternatively or in addition, the delivery wire 4 with the clot-retriever 3 can also be forwarded distally for the deployment.

Figure 25E:
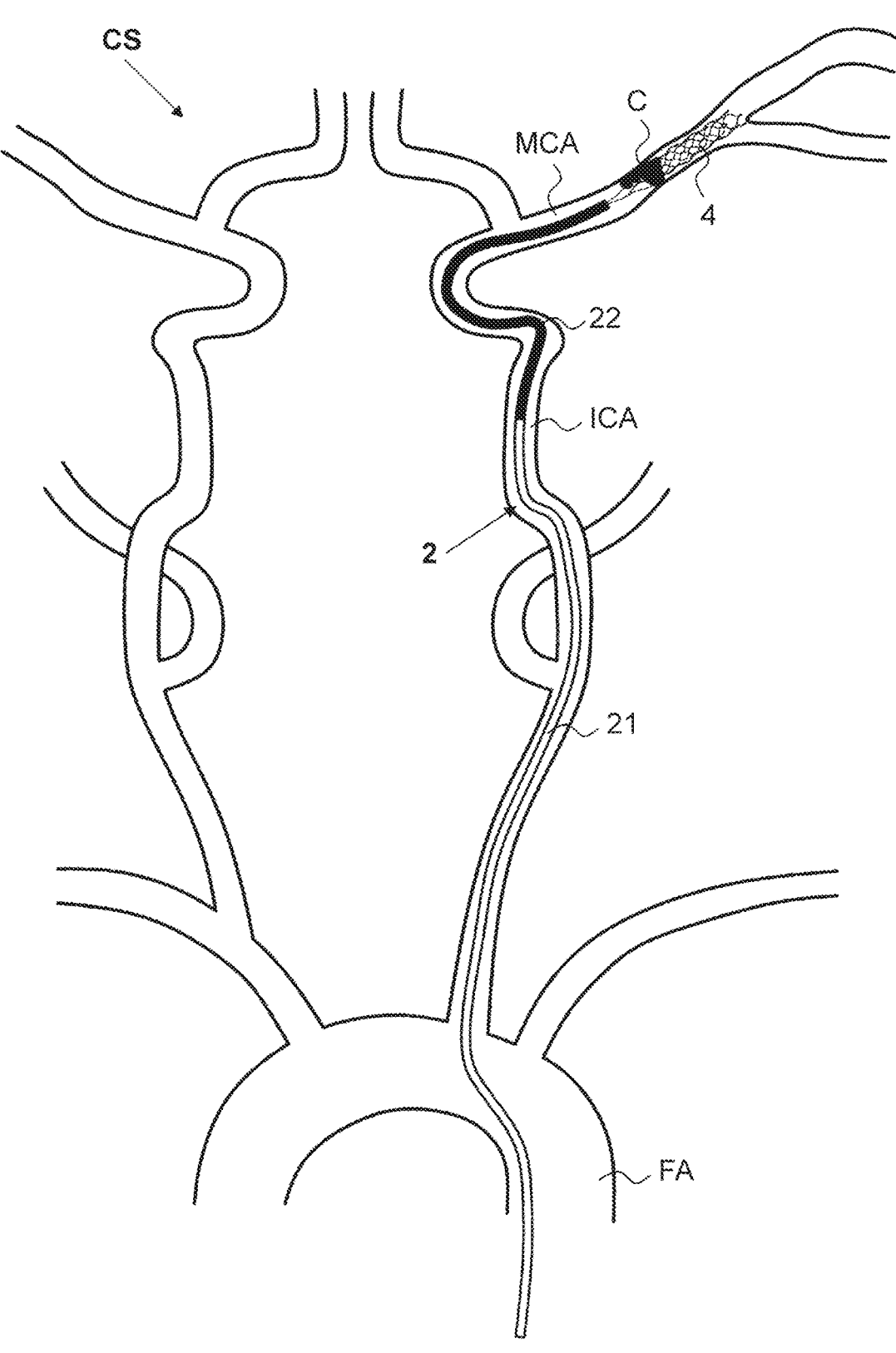
FIG. 25e schematically shows the catheter of FIGS. 25b, 25c and 25d, in expanded state and ready to aspirate the clot.

For enabling clot aspiration through the catheter 2, the distal outer section 22 is then brought from its unexpanded in its expanded state and the distal opening 221 is positioned directly proximal of the clot C, as shown in FIGS. 24d and 25e.

Figure 25F:
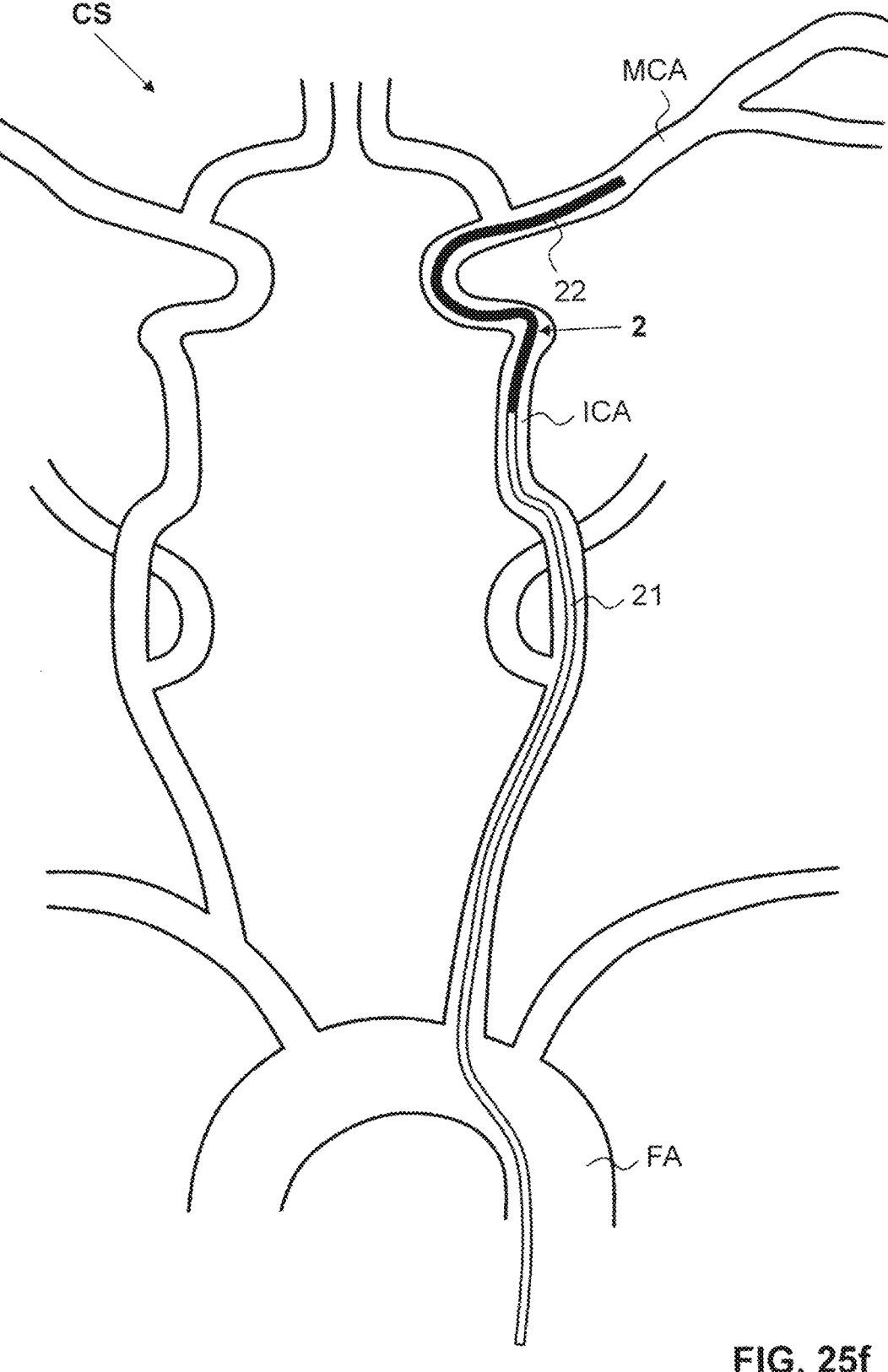
FIG. 25f schematically shows the catheter of FIGS. 25b, 25c and 25d, in expanded state, after retracting the clot-retriever and the clot under the application of an aspiration force into the catheter.

In the step shown in FIGS. 24e and 25f, the delivery wire 4 with the clot-retriever 3 and the clot C is retracted into the catheter 2. At the same time, aspiration of the clot C through the catheter 2 is applied, in order to support the retraction process.

Finally, the catheter 2 is completely retracted from the circulatory system, with the clot C held by both the clot-retriever 3 and the vacuum which is preferably still applied within the inner lumen of the catheter.

LIST OF REFERENCE SIGNS

| | |
|---|---|
| CS | Circulatory system |
| FA | Femoral artery |
| ICA | Internal carotid artery |
| MCA | Middle cerebral artery |
| BV | Blood Vessel |
| C | Clot |
| 1 | Guide wire |
| 2 | Catheter |
| 21 | Proximal outer section |
| 22 | Distal outer section |
| 221 | Distal end |
| 222 | Reinforcement element |
| 223 | Hull |
| 224 | Reinforcing wire |
| 225 | Semi-cylindrical spring structure |
| 226 | Spring clip |
| 227 | Loop |
| 228 | Hooked element |
| 229 | Attachment element |
| 23 | Inner tubular element |
| 231 | Coil |
| 24 | Pull element |
| 25 | Push element |
| 251 | Receiver cylinder |
| 252 | Widened end |
| 253 | Loop |
| 254 | Coil spring |
| 26 | Coiled thread |
| 27 | Trailing wire |
| 3 | Stent retriever |
| 4 | Delivery wire |
| D1 | First diameter |
| D2 | Second diameter |

What is claimed:

1. A method for endoluminal intervention at a target site in a patient's vasculature, the method comprising:

pushing a distal braided section of an outer catheter tube having a proximal section, via an inner push tube extending through the proximal section and the distal braided section, to extend the distal braided section to stretch longitudinally and contract radially to an unexpanded state, wherein the inner push tube is coupled to the distal braided section via a spring element coupled to the distal braided section;

advancing the distal braided section in the unexpanded state to the target site while the inner push tube extends through the proximal section and the distal braided section; and actuating the inner push tube to cause the distal braided section to transition from the unexpanded state to a radially expanded state at the target site in the patient's vasculature for performing the endoluminal intervention.

2. The method of claim 1, wherein actuating the inner push tube comprises pulling the inner push tube proximally to cause the distal braided section to transition from the unexpanded state to the radially expanded state.

3. The method of claim 1, further comprising, after causing the distal braided section to transition to the radially expanded state, removing the inner push tube from the outer catheter tube.

4. The method of claim 1, wherein performing the endoluminal intervention comprises removing one or more clots through the outer catheter tube while the distal braided section is in the radially expanded state.

5. The method of claim 4, wherein removing the one or more clots comprises aspirating the one or more clots while the distal braided section is in the radially expanded state.

6. The method of claim 4, further comprising, after removing the one or more clots, moving the distal braided section of the outer catheter tube to one or more additional clots in the patient's vasculature; and removing the one or more additional clots through the outer catheter tube while the distal braided section is in the radially expanded state.

7. The method of claim 4, wherein removing the one or more clots comprises removing the one or more clots in the patient's neurovasculature to treat ischemic stroke.

8. The method of claim 1, wherein removing the one or more clots comprises advancing a clot-retriever through the outer catheter tube to engage with the one or more clots to remove the one or more clots via the clot-retriever.

9. The method of claim 1, wherein the spring element comprises a clip.

10. The method of claim 1, wherein the spring element comprises a semi-cylindrical structure.

11. The method of claim 1, wherein the spring element is coupled to a distal end of the distal braided section.

12. The method of claim 1, wherein the inner push tube is coupled to a distal end of the distal braided section via the spring element.

13. The method of claim 1, further comprising an inner elongated tube configured to be disposed within the outer catheter tube, the inner elongated tube longitudinally moveable relative to the distal braided section of the outer catheter tube.

14. The method of claim 1, wherein performing the intervention comprises advancing a device through the outer catheter tube to the target site.

15. The method of claim 14, wherein the device comprises a clot-retriever.

16. The method of claim 1, wherein, in the radially expanded state, the distal braided section's diameter is the same or less than the proximal section's diameter.

17. The method of claim 1, wherein the distal braided section comprises a coating.

18. The method of claim 1, wherein the coating comprises a lubricious coating on an outer surface on the distal braided section.

19. The method of claim 1, wherein the distal braided section comprises nitinol.

20. The method of claim 19, wherein the distal braided section comprises an outer hull having a radial elasticity.

21. The method of claim 20, wherein the outer hull comprises a polymer.

22. The method of claim 1, further comprising a PTFE coating.

23. A method for endoluminal intervention to remove one or more clots in a patient's vasculature, the method comprising:

pushing a distal braided section of an outer catheter tube having a proximal section, via an inner push tube extending through the proximal section and the distal braided section, to extend the distal braided section to stretch longitudinally and contract radially to an unexpanded state, wherein the inner push tube is coupled to the distal braided section via a spring element coupled to the distal braided section;

advancing the distal braided section in the unexpanded state to the one or more clots in the patient's vasculature while the inner push tube extends through the proximal section and the distal braided section;

pulling the inner push tube proximally to cause the distal braided section to transition from the unexpanded state to a radially expanded state;

removing the inner push tube from the outer catheter tube; and removing the one or more clots through the outer catheter tube while the distal braided section is in the radially expanded state.

24. The method of claim 23, wherein removing the one or more clots comprises aspirating the one or more clots while the distal braided section is in the radially expanded state.

25. The method of claim 23, further comprising, after removing the one or more clots, moving the distal braided section of the outer catheter tube to one or more additional clots in the patient's neurovasculature; and removing the one or more additional clots through the outer catheter tube while the distal braided section is in the radially expanded state.

26. The method of claim 23, wherein removing the one or more clots comprises removing the one or more clots in the patient's neurovasculature to treat ischemic stroke.

27. The method of claim 23, wherein the inner push tube is coupled to a distal end of the distal braided section via the spring element.

28. The method of claim 23, wherein the spring element comprises a clip or a semi-cylindrical structure.

* * * * *